United States Patent
Chen et al.

(10) Patent No.: US 10,323,035 B2
(45) Date of Patent: Jun. 18, 2019

(54) CO-CRYSTAL OF A CDK INHIBITOR AND AN MEK INHIBITOR AND PROCESS OF PREPARATION THEREOF

(71) Applicant: CRYSTAL PHARMATECH CO., LTD, Suzhou, Jiangsu (CN)

(72) Inventors: Minhua Chen, Jiangsu (CN); Yanfeng Zhang, Suzhou (CN); Qiyue Liu, Jiangsu (CN); Nan Xia, Jiangsu (CN); Chaohui Yang, Jiangsu (CN); Xiaoyu Zhang, Jiangsu (CN)

(73) Assignee: Crystal Pharmatech Co., Ltd., Suzhou, Jiangsu (CN)

( * ) Notice: Subject to any disclaimer, the term of this patent is extended or adjusted under 35 U.S.C. 154(b) by 0 days.

(21) Appl. No.: 15/563,344

(22) PCT Filed: Apr. 1, 2016

(86) PCT No.: PCT/CN2016/078400
§ 371 (c)(1),
(2) Date: Sep. 29, 2017

(87) PCT Pub. No.: WO2016/155670
PCT Pub. Date: Oct. 6, 2016

(65) Prior Publication Data
US 2018/0057498 A1   Mar. 1, 2018

(30) Foreign Application Priority Data

Apr. 1, 2015  (CN) .......................... 2015 1 0152042
Nov. 18, 2015  (CN) .......................... 2015 1 0794226

(51) Int. Cl.
*C07D 487/04*  (2006.01)
*A61K 31/4184*  (2006.01)
*A61K 31/519*  (2006.01)
*C07D 235/06*  (2006.01)

(52) U.S. Cl.
CPC ........ *C07D 487/04* (2013.01); *A61K 31/4184* (2013.01); *A61K 31/519* (2013.01); *C07D 235/06* (2013.01); *C07B 2200/13* (2013.01)

(58) Field of Classification Search
CPC .................................................. C07D 487/04
USPC ....................................................... 544/280
See application file for complete search history.

(56) References Cited

U.S. PATENT DOCUMENTS

2010/0204204 A1* 8/2010 Zaworotko ............ A61K 31/20
514/212.03

FOREIGN PATENT DOCUMENTS

| CN | 103201275 A | 7/2013 |
| WO | 2012064805 | 5/2012 |
| WO | 2014/097125 A1 * | 6/2014 |
| WO | 2014097125 A1 | 6/2014 |

OTHER PUBLICATIONS

Yadav et al., Indian J. Pharm. Sci. (2009) vol. 71(4), pp. 359-370.*
Sun et al., J. Chem. and Eng. Data, 2015, 60, 1166-1172.*

* cited by examiner

*Primary Examiner* — Taofiq A Solola
(74) *Attorney, Agent, or Firm* — VLP Law Group LLP; Kent H. Cheng

(57) ABSTRACT

The present disclosure relates to novel co-crystals of a CDK inhibitor and an MEK inhibitor and the preparation methods thereof. Specifically, the present disclosure provides hydrates or anhydrates which are named as Form I, Form II and Form III. The novel co-crystals provided in the present disclosure have good stability, low hygroscopicity and high solubility, and have an important value for further optimization and development of the drug.

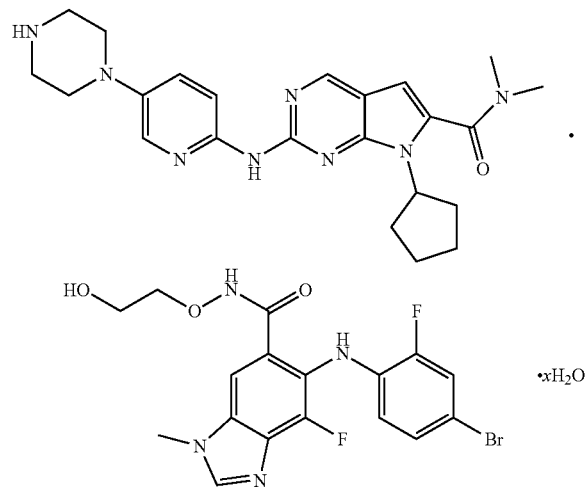

19 Claims, 12 Drawing Sheets

CO-CRYSTAL OF A CDK INHIBITOR AND AN MEK INHIBITOR AND PROCESS OF PREPARATION THEREOF

TECHNICAL FIELD

The present disclosure relates to the field of pharmaceutical chemistry, particularly relates to co-crystal of a CDK inhibitor (LEE011) and an MEK inhibitor (MEK162) and process of preparation thereof.

BACKGROUND

With the continuous occurrence of drug resistance in melanoma, combination therapy of multi-targets drug has become the main development direction of targeted therapy. NRAS gene mutation is a common type of genetic variation in patients with skin malignant melanoma, which accounts for about 20%. The patients with NRAS gene mutation have poorer prognosis and specific targeted therapy drugs are lacked. Research shows that in the NRAS mutated melanoma cells, the MAPK signal pathway is activated abnormally, and there are much cell cycle checkpoint disorders. Therefore, it may have a synergistic anti-tumor effect and enhance the anti-tumor effect when inhibiting MAPK Signal Pathway Key molecule MEK and the cell cycle key regulation kinase CDK4/6 at the same time.

Novartis announced the Phase I clinical data of treating the NRAS mutated melanoma with combination therapy of the CDK inhibitor LEE011 (Ribociclib) and the MEK inhibitor MEK162 (Binimetinib) and the data showed a good clinical effect. At present, Phase II clinical trial for this combination is ongoing.

LEE011 is a cyclin-dependent kinase 4/6 (CDK4/6) inhibitors which is for the treatment of drug-resistant breast cancer and melanoma. It has a good performance in clinical study and has received positive clinical results. Currently it is in phase III clinical studies. The chemical name of LEE011 is 7-Cyclopentyl-2-(5-piperazin-1-yl-pyridin-2-ylamino)-7H-pyrrolo [2, 3-D]pyrimidine-6-carboxylic acid dimethylamide, and the structure is shown as formula (Ia):

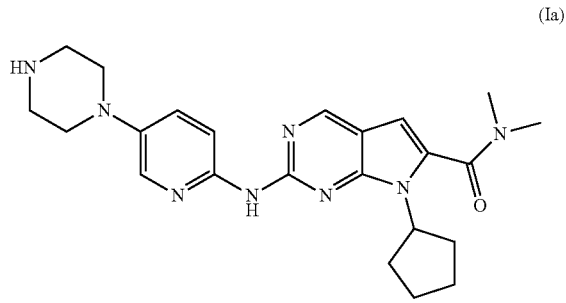 [SMILES: CN(C)C(=O)c1cc2cnc(Nc3ccc(N4CCNCC4)cn3)nc2n1C1CCCC1]

(Ia)

MEK162 is an oral mitogen-activated protein kinase (MEK) inhibitor and is currently in Phase III clinical trials in the United States for the treatment of NRAS mutated melanoma, BRAF mutated melanoma and recurrent low-level plasma ovarian cancer. The chemical name of MEK162 is 5-[(4-bromo-2-fluorophenyl) amino]-4-fluoro-N-(2-hydroxyethoxy)-1-methyl-1H-benzimidazol-6-carboxamide, and the structure is shown as formula (Ib):

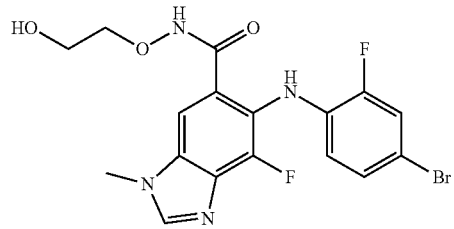

(Ib)

WO2014097125A1 discloses the combination of LEE011 and MEK162, but the combination is a physical mixture of the two components and the two components do not form a co-crystal which is essentially different from the present disclosure.

Pharmaceutical co-crystal is a co-crystal structure comprising two components. The interaction between the two components is generally non-covalent interactions (such as hydrogen bonding, π-π interactions, halogen bonding, etc.). The formation of the pharmaceutical co-crystal generally does not destroy the covalent bonding of active pharmaceutical ingredient. There are reports show that through forming a co-crystal the drug has the opportunity to improve the crystallization properties and physicochemical properties such as bioavailability (Pharmaceut. Res. 23(8), 2006, pp. 1888-1897.), stability and processibility (Int. J. Pham. 320, 2006, pp. 114-123.). Therefore, Pharmaceutical co-crystal is a new choice for the solid pharmaceutical preparations.

In prior art, the pharmaceutical co-crystal is usually formed of active pharmaceutical ingredient and co-crystal former, and the active pharmaceutical ingredient is usually a good donor or a receptor compound that has more rigid structure, higher symmetry, lower molecular weight and contains protons. While the co-crystal reagents are mostly pharmaceutical excipients, vitamins, amino acids and food additives. Currently, no research has reported about the co-crystals of the two drugs and their therapeutic effect, particularly there is no report about co-crystal of the two active pharmaceutical ingredients of LEE011 and MEK162.

SUMMARY

The present disclosure of co-crystals of LEE011 and MEK162 is surprisingly discovered by a large amount of experiments, and the co-crystals have advantages that are suitable for production and use.

One objective of the disclosure is to provide co-crystals of LEE011 and MEK162. The novel co-crystals provided in the present disclosure have good stability, low hygroscopicity, and compared with the physical mixture of equimolar LEE011 and MEK162, both components in co-crystals have faster dissolution rate and higher solubility.

Another objective of the present disclosure is to provide processes of preparing the co-crystals. Although the present co-crystals may be obtained by other methods, the present processes of preparing the co-crystals is simple, low cost, and have an important value for clinical optimization and development of the combination of LEE011 and MEK162.

In order to achieve the above object, the present disclosure uses the following technical solution:

A co-crystal of a CDK inhibitor (LEE011) and an MEK inhibitor (MEK162), the structure of the co-crystal is shown as formula (I):

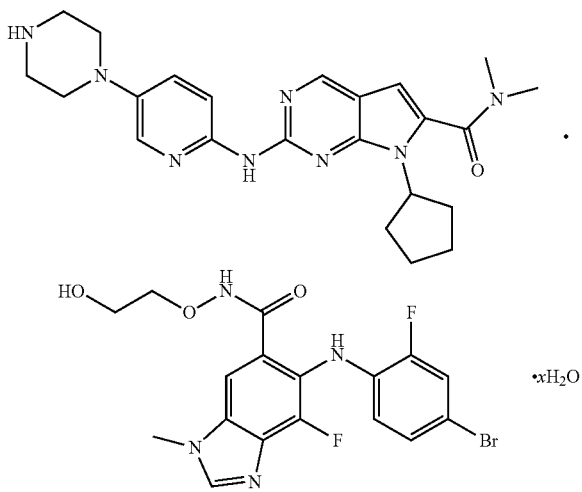

(I)

·xH₂O

In the formula, x is a number between 0-3. X represents the molar number of water involved in the crystal lattice. When x is 0, the co-crystal is anhydrous. When x is larger than 0, the co-crystal is hydrate. The value of x can be an integer or a non-integer.

Preferably, x is 0, 1, 2 or 3.

According to the present disclosure, when referring to "co-crystal", the interaction between LEE011 and MEK162 is not only included non-covalent interactions such as hydrogen bonding but also included other covalent bonding or combination thereof. It belongs to the scope of the disclosure as long as the two drug molecules are combined to form a co-crystal, regardless of what forms their binding force are.

According to one embodiment of the present disclosure, this disclosure provides a hydrate form named Form I. The X-ray powder diffraction pattern using CuKα radiation of this Form I shows characteristic peaks at 2theta values of 19.3°±0.2°, 22.7°±0.2° and 10.4°±0.2°. According to a preferred embodiment, the X-ray powder diffraction pattern of Form I shows one or more characteristic peaks at 2theta values of 11.4°±0.2°, 23.6°±0.2° and 13.4°±0.2°.

According to one embodiment, the X-ray powder diffraction pattern of Form I shows characteristic peaks at 2theta values of 11.4°±0.2°, 23.6°±0.2° and 13.4°±0.2°.

According to another preferred embodiment, the X-ray powder diffraction pattern of Form I shows one or more characteristic peaks at 2theta values of 21.6°±0.2°, 26.0°±0.2° and 8.3°±0.20. According to one embodiment, the X-ray powder diffraction pattern of Form I shows characteristic peaks at 2theta values of 21.6°±0.2°, 26.0°±0.2° and 8.3°±0.2°.

According to the third preferred embodiment, the X-ray powder diffraction pattern of Form I shows one or more characteristic peaks at 2theta values of 11.4°±0.2°, 23.6°±0.2°, 13.4°±0.2°, 21.6°±0.2°, 26.0°±0.2° and 8.3°±0.2°.

According to one of the most preferred embodiment, the X-ray powder diffraction pattern of Form I shows all characteristic peaks at 2theta values of 11.4°±0.2°, 23.6°±0.2°, 13.4°±0.2°, 21.6°±0.2°, 26.0°±0.2° and 8.3°±0.2°. In a specific embodiment according to this project, the X-ray powder diffraction pattern of Form I is substantially depicted in FIG. 1.

According to the present disclosure, the water content (or x value) in the said Form I is preferred between 0.5~3 moles. According to a specific embodiment, the water content (or x value) in Form I is 3 moles.

More preferably, Form I of the present disclosure shows first endothermic peak when heated to around 86~95° C. and shows second endothermic peak when heated to around 130~142° C. The differential scanning calorimetry (DSC) thermogram of Form I is substantially as depicted in FIG. 2.

More preferably, Form I of the present disclosure shows about 5~6% weight loss when heated to around 110° C. The thermal gravimetric analysis (TGA) thermogram of Form I is substantially as depicted in FIG. 3.

According to another specific embodiment of the present disclosure, this disclosure provides a anhydrate form, named Form II. The X-ray powder diffraction pattern using CuKα radiation of Form II shows characteristic peaks at 2theta values of 13.1°±0.2°, 10.3°±0.2° and 16.4°±0.2°. According to a preferred embodiment, the X-ray powder diffraction pattern of Form II of the present disclosure shows one or more characteristic peaks at 2theta values of 19.1°±0.2°, 21.9°±0.2° and 14.8°±0.2°. According to one embodiment, the X-ray powder diffraction pattern of Form II shows characteristic peaks at 2theta values of 19.1°±0.2°, 21.9°±0.2° and 14.80°±0.2°.

According to another embodiment, the X-ray powder diffraction pattern of Form II of the present disclosure shows one or more characteristic peaks at 2theta values of 20.4°±0.2°, 15.10°±0.2° and 19.7°±0.2°. According to one embodiment, the X-ray powder diffraction pattern of Form II of the present disclosure shows characteristic peaks at 2theta values of 20.4°±0.2°, 15.1°±0.2° and 19.7°±0.2°.

According to the third preferred embodiment, the X-ray powder diffraction pattern of Form II of the present disclosure shows one or more characteristic peaks at 2theta values of 19.10°±0.2°, 21.90°±0.2θ, 14.8°±0.2°, 20.4°±0.2°, 15.1°±0.2° and 19.7°±0.2°.

According to one of the most preferred embodiments, the X-ray powder diffraction pattern of Form II of the present disclosure shows all characteristic peaks at 2theta values of 19.10°±0.2°, 21.9°±0.2°, 14.8°±0.2°, 20.4°±0.2°, 15.1°±0.2° and 19.7°±0.2°. In a specific embodiment according to this project, the X-ray powder diffraction pattern of Form II is substantially depicted in FIG. 4.

More preferably, Form II of the present disclosure shows an endothermic peak when heated to around 132~146° C. and the differential scanning calorimetry (DSC) thermogram of Form II is substantially as depicted in FIG. 5.

More preferably, Form II of the present disclosure shows about 2.6~2.9% weight loss when heated to around 130° C. The thermal gravimetric analysis (TGA) thermogram of Form II is substantially as depicted in FIG. 6.

In the present disclosure, as shown in FIG. 5 and FIG. 6, there is little weight loss in TGA and no desolvation or dehydration peak in DSC, thus, the Form II is speculated to be an anhydrate.

In the present disclosure, since Form II can be obtained by heating co-crystal Form I, when the heating temperature is beyond the melting point, the mole ratio of co-crystal Form II is same as Form I.

According to another embodiment of the present disclosure, this disclosure provides a hydrate form named Form III. The X-ray powder diffraction pattern using CuKα radiation of this Form III shows characteristic peaks at 2theta values of 18.8°±0.2°, 20.5°±0.2° and 23.1°±0.2°.

According to a preferred embodiment, the X-ray powder diffraction pattern of Form III of the present disclosure shows one or more characteristic peaks at 2theta values of 22.6° 00.2°, 4.3°±0.2° and 12.7°±0.2°. According to a specific embodiment, the X-ray powder diffraction pattern of Form III of the present disclosure shows characteristic peaks at 2theta values of 22.6°±0.2°, 4.3°±0.2° and 12.7° 00.2°.

According to another preferred embodiment, the X-ray powder diffraction pattern of Form III of the present disclosure shows one or more characteristic peaks at 2theta values of 26.2θ±0.2θ, 24.7°±0.2° and 21.6°±0.2°. According to a specific embodiment, the X-ray powder diffraction pattern of Form III of the present disclosure shows all characteristic peaks at 2theta values of 26.2°±0.2θ, 24.7°±0.2° and 21.6°±0.2°.

According to third preferred embodiment, the X-ray powder diffraction pattern of Form III of the present disclosure shows one or more characteristic peaks at 2theta values of 22.6°±0.2°, 4.3°±0.2°, 12.70°±0.2°, 26.2°±0.2°, 24.7°+0.2° and 21.6°±0.2θ.

According to one of the most preferred embodiments, the X-ray powder diffraction pattern of Form III of the present disclosure shows characteristic peaks at 2theta values of 22.6°±0.2°, 4.3°±0.2°, 12.7°±0.2°, 26.2°±0.2°, 24.7°±0.2° and 21.6°±0.2°. In a specific embodiment according to this project, the X-ray powder diffraction pattern of Form III is substantially depicted in FIG. 7, and there are 41 characteristic peaks in it, and the position and peak intensity of characteristic peaks are displayed in Table 5. In another specific embodiment according to this project, the X-ray powder diffraction pattern of Form III shows 38 characteristic peaks, and the position and peak intensity of characteristic peaks are displayed in Table 6. In another specific embodiment according to this project, the X-ray powder diffraction pattern of Form III shows 29 characteristic peaks, and the position and peak intensity of characteristic peaks are displayed in Table 7.

More preferably, Form II I of the present disclosure shows first endothermic peak when heated to around 70~78° C. and shows second endothermic peak when heated to around 114~126° C.

The differential scanning calorimetry (DSC) thermogram of Form III is substantially as depicted in FIG. 8.

More preferably, Form III of the present disclosure shows about 4.4~4.8% weight loss when heated to around 114° C. The thermal gravimetric analysis (TGA) thermogram of Form III is as depicted in FIG. 9.

According to the disclosure, the water content (or x value) in Form III is preferred between 0.5~3 moles. More preferred the water content is between 2~3 moles. Further preferred, the water content is 2 moles or 3 moles, and 2 moles is most preferred.

Another objective of the present disclosure is providing a single crystal of the co-crystal of a CDK inhibitor and an MEK inhibitor, and the said co-crystal is Form I. The single crystal of the co-crystal is a colorless transparent long rod-shaped crystal, and belongs to monoclinic crystal system. The space group of Form I is $P2_1/c$, and the unit cell dimensions are a=7.3±0.2 Å, b=23.3±0.2 Å, c=25.6±0.2 Å, α=90°, β=106.0±0.2°, γ=90°.

Preferably, the unit cell dimensions of this single crystal are a=7.2~7.3 Å, b=23.3~23.4 Å, c=25.6~25.7 Å, α=90°, β=105.95~106.05°, γ=90°. In particular, the unit cell dimensions of this single crystal are a=7.28~7.29 Å, b=23.34~23.35 Å, c=25.61~25.62 Å, α=90°, β=105.99~106.1°, γ=90°. More specifically, the unit cell dimensions of this single crystal are a=7.284~7.285 Å, b=23.348~23.350 Å, c=25.6111~25.613 Å, α=90°, β=105.999~106.001° and γ=90°. In a specific embodiment, the unit cell dimensions are a=7.2846(13) Å, b=23.349(4) Å, c=25.612(5) Å; α=90°, β=106.000(6)°, γ=900.

According to a specific embodiment of the present disclosure, the asymmetric structural unit of this co-crystal single crystal contains a anion or molecule of MEK162, a cation or molecule of LEE011, three water molecules; the unit cell of this crystal contains four anions or molecules of MEK162, four cations or molecules of LEE011, twelve water molecules; its asymmetric structural unit is depicted in FIG. 22 and the schematic diagram of unit cell is depicted in FIG. 23.

Another objective of the present disclosure is to provide a process of the preparing said co-crystals: LEE011 and MEK162 are mixed in a solvent system of one or more organic solvents of alcohols, ketones, ethers, nitriles and water, then the said co-crystals are obtained by evaporation, stirring or cooling.

Preferably, LEE011 and MEK162 are mixed in the said solvent system at 0~50° C.

Furthermore, the said alcohols include but are not limited to methanol, ethanol and isopropyl alcohol; the said ketones include but are not limited to acetone, methyl ethyl ketone and methyl isobutyl ketone; the said ethers include but are not limited to cyclic ethers and alkyl ethers, such as tetrahydrofuran, 1, 4-dioxane and methyl tert-butyl ether of alkyl ethers; the said nitriles include but are not limited to acetonitrile.

Preferably, the said solvent system is one or more solvents of acetonitrile, ethanol, methanol and water.

According to the present disclosure, when the said solvent system is a mixture of water and acetonitrile or a mixture of water and ethanol, the obtained co-crystal is Form I; when the said solvent system is methanol, the obtained co-crystal is Form III.

Furthermore, said Form II is obtained by dehydrating Form I according to one embodiment of the present disclosure, this disclosure also provides a process for the preparation of said co-crystal: LEE011 and MEK162 are mixed in a solvent containing water, then the Form I is obtained by evaporation, stirring or cooling.

Preferably, the said solvent containing water is a solvent of water and alcohols or a solvent of water and nitriles.

More preferably, the said solvent containing water is a solvent of water and ethanol or a solvent of water and acetonitrile.

In the present disclosure, there is no special limitation on the mixing ratio of organic solvents and water, the inventors use a mixture of various proportions in the experiments, and the Form I can be well obtained.

Preferably, said LEE011 and said MEK162 are mixed in the said solvent containing water at a temperature of 0~50° C.

Preferably, the content of MEK162 in solvent containing water is 6~10 mg/mL.

Preferably, the mass ratio of LEE011 and MEK162 is 1:0.9~2.

According to another embodiment of the present disclosure, this disclosure further provides a process for the preparation of said co-crystal, the preparation of Form II includes step 1 or step 2:
Step 1: Form II is obtained by dehydrating Form I prepared according to process of the present disclosure.
Step 2: LEEI011 and MEK162 are mixed in an organic solvent, and the Form II is obtained by evaporation, stirring or cooling.

Preferably, in the step 1, the said dehydrating is at a temperature of 130~140° C.

Preferably, in the step 2, the said organic solvent is acetonitrile or ethanol.

According to the third embodiment of the present disclosure, this disclosure further provides a process for the preparation of said co-crystal, the preparation of Form III includes step 1 or step 2:
Step 1: Form I prepared according to the process of the present disclosure is mixed in an alcohol solvents or a mixed solvent system of alcohol with water, alcohol, ether or nitrile, and then Form III is obtain by evaporation Step 2: LEE011 and MEK162 are mixed in alcohol organic solvents, then the Form III is obtain by evaporation.

Preferably, in the step 1, the content of Form I in alcohol solvents or a mixed solvent of alcohols with water, alcohols, ethers or nitriles in step 1 is 8~25 mg/mL Preferably, in the step 1, Form I is mixed in alcohol organic solvents, and the Form III can be obtained by evaporation.

More preferably, the said alcohol organic solvents contain methanol.

Preferably, in the step 2, the mass ratio of LEE011 and MEK62 in step 2 is 1:0.9~1.1. Preferably, in the step 2, the content of MEK162 in alcohol solvents in step 2 ratio of the feed quality of MEK162 and the volume of alcohol solvents in step 2 is 6~7 mg/mL.

The third objective of the disclosure is to provide a pharmaceutical composition, and the composition comprises an active ingredient and a pharmaceutically acceptable excipient, wherein the active ingredient comprises said co-crystal.

According to one embodiment of the present disclosure, the present disclosure provides a pharmaceutical composition comprising the active ingredient and a pharmaceutically acceptable excipient, said active ingredient comprises one or more of crystalline Form I, crystalline Form II, crystalline Form III.

The forth objective of the disclosure is to provide a use of the co-crystals in preparation of a drug for treating cancer.

According to one embodiment of the present disclosure, the disclosure is to provide a use of one or more of crystalline Form I, crystalline Form II, crystalline Form III in preparation of a drug for treating cancer.

The fifth objective of the present disclosure is to provide a use of the co-crystal in the treatment of cancer.

The sixth objective of the disclosure is to provide a method for treating cancer. The method comprises the step of applying the co-crystals or a pharmaceutical composition as described above to the patient.

Furthermore, the cancer includes but not limited to melanoma, pancreatic cancer, ovarian cancer, breast cancer, lymphoma and lung cancer.

The advantages of the present disclosure are as follows:
The present disclosure provides the co-crystals of LEE011 and MEK162 and these co-crystals have good performances in bioavailability, therapeutic effects, stability, processibility and storage, especially their therapeutic effect is better than the physical mixture of LEE011 and MEK162.

DETAILED DESCRIPTION

Figure 1:
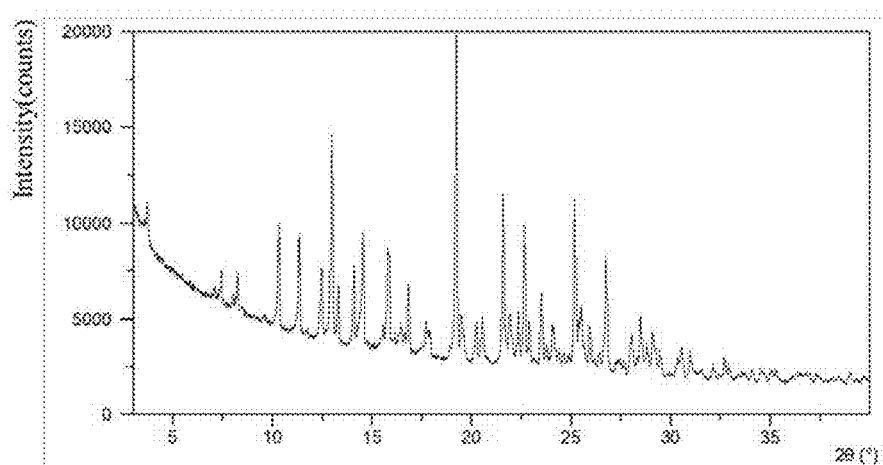
FIG. 1 shows an XRPD pattern of crystalline Form I obtained in Example 1.

The present disclosure will be further explained by the specific embodiments and the specific embodiments are not intended to limit the scope of the present disclosure. The skilled in the art can make improvements to the process of preparation and the used instruments within the scope of the claims, and those improvements should be considered as falling into the scope of the present disclosure. Therefore, the protective scope of the present disclosure patent should be defined by the claims. Raw material as LEE011 and MEK162 free form used in process of preparing is prepared by known methods.

In the process of preparing crystalline forms of the present disclosure:

The "room temperature" refers to 15~25° C.

The "stirring" is completed by using a conventional method in the field such as a mechanical stirring or a magnetic stirring and the stirring speed is 50 to 1800 r/min, preferably 300 to 900 r/min.

The "separation" is completed by using a conventional method in the field such as centrifugation or filtration. The operation of "centrifugation" is as follows: the sample to be separated is placed into the centrifuge tube, then centrifugated at a rate of 10000 r/min until the solid all sink to the bottom of the tube.

Unless otherwise specified, said "drying" can be carried out at room temperature or a higher temperature. The drying temperature is from room temperature to about 60° C., or to 40° C., or to 50° C. The drying time can be 2 to 48 hours, or overnight. Drying is carried out in a fume hood, oven or vacuum oven.

In the present disclosure, "Crystal" or "Crystalline Form" refers to the crystal or the crystal form being identified by the X-ray diffraction pattern shown herein. The scientists in this art are able to understand that physical and chemical properties discussed herein can be characterized and the experimental errors depend on the conditions of instruments, the sample preparations and the purity of samples. In particular, the scientists in this field generally know that the X-ray diffraction pattern usually may change with the change of the experimental conditions. It is necessary to point out that, the relative intensity of the X-ray diffraction pattern is likely to change with the change of the experimental conditions; therefore, the sequence of peak intensity cannot be regarded as the only or the determining factor. Moreover, the experimental errors of the peak angles are 5% or less, so such errors shall be considered and generally the allowed errors are ±0.2° 2θ. In addition, due to the effect of the experimental factors including sample height, peak angles may have an overall shifting; generally, certain shifting is allowed. Hence, the scientists in this field may understand that, it is unnecessary that the X-ray diffraction pattern of a crystal form in the present disclosure should be exactly the same with X-ray diffraction patterns of the example shown herein. Any crystal forms whose X-ray diffraction pattern have the same or similar characteristic peaks should be within the scope of the present disclosure. The scientists in this field can compare the patterns shown in the present disclosure with that of an unknown crystal form in order to identify whether these two groups of patterns reflect the same or different crystal forms.

"Crystalline Form" and "Polymorphic Form" as well as other related terms in the present disclosure refer to the solid compounds whose crystal structure is being in a special crystal form state. The difference in the physical and chemical properties of the polymorphic forms may be embodied in storage stability, compressibility, density, dissolution rate, etc. In extreme cases, the difference in solubility or dissolution rate may result in inefficient drugs, even developing toxicities.

Pharmaceutical co-crystal is a co-crystal structure comprising two components. The interaction between the two components is generally non-covalent interactions (such as hydrogen bonding, π-π interactions, halogen bonding, etc.). The formation of the pharmaceutical co-crystal generally doesn't destroy the covalent bonding of pharmaceutically active ingredient. The term "effective treatment amount" or "therapeutically effective amount" as used herein means that amount of an active compound that elicits the biological or medicinal response in a tissue, system, animal or human that is being sought by a researcher, veterinarian, medical doctor, or other clinician.

As used herein, the term "treatment" refers to one or more of the following: (1) Preventing disease, for example, preventing the disease, illness or disorder in an individual who may be suffering from a disease, illness or disorder but not suffering from or displaying a lesion or symptom of the disease, (2) Inhibiting the disease, for example, inhibiting the disease, illness or disorder in an individual who is suffering from or displaying a lesion or symptom of the disease, illness or disorder, and (3) Improving the disease, for example, improving the disease, illness or disorder in an individual who is suffering from or displaying a lesion or symptom of the disease, illness or disorder (that is to reverse the lesion and/or symptoms), for example, reducing the severity of the disease.

In some embodiments, the new crystalline forms of the present disclosure are pure, single, substantially no mixing any other crystalline form. In the present disclosure, the term "substantially free" when used to refer to a new crystalline form refers to the another crystalline form contained less than 20% (by weight), but also refers to the new less than 10% (by weight), in particular It means less than 5% (by weight), and particularly to less than 1% (by weight).

It should be noted that the numerical value and the scope of the present disclosure should not be narrowly understood as a value or numerical value range. It should be understood by those skilled in the art that the specific numerical value can be floated according to the specific technical environment on the basis that the spirit and principle of the disclosure are not depart from the spirit and principle of the disclosure. In the present disclosure, the number of floating ranges which can be expected by one of skilled in the art is represented by the term "about".

The polymorphic forms of drugs may be obtained by the methods including but not limited to the following: melting and recrystallization, melting and cooling, solvent recrystallization, desolvation, rapid volatilization, rapid cooling, slow cooling, vapor diffusion and sublimation. The polymorphic form may be tested, discovered and classified via X-ray powder diffraction (XRPD), differential scanning calorimetry (DSC), thermo gravimetric analysis (TGA), optical microscopy, hygroscopicity, etc. The crystallization methods for the crystal forms of the present disclosure include evaporation, slurry and cooling.

Furthermore, the present disclosure provides a pharmaceutical composition, the pharmaceutical composition comprises a therapeutically and/or prophylactically effective amount of co-crystals of the present disclosure, and at least one pharmaceutically acceptable excipient. The co-crystal above can be one or more of Form I, Form II and Form III. In addition, the pharmaceutical compositions can also contain other pharmaceutically acceptable co-crystal salts, the crystalline form or amorphous substance of the salt. Optionally, the crystalline forms of the present disclosure may be administered as the sole active agent, or they may be administered in combination with other active agents that have the same or a similar therapeutic activity, and such a combination is administered for other compounds identified as safe and effective. In a particular embodiment, the administered in combination of two (or more) active agents can significantly reduce the dose of each active agent used and reduce the side effects.

The pharmaceutical composition can be developed into a certain dosage form, and is administrated by a suitable route, such as oral administration and parenteral administration (including subcutaneous, muscle, vein or skin), rectal, transdermal, nasal and vagina, and the like. The dosage form suitable for oral administration comprises tablets, capsules, granules, powder and pills, a powder, an ingot, a solution, a syrup or a suspension according to needs, and can be used for rapid release, delayed release or regulation release of active pharmaceutical ingredients. The dosage form suitable for parenteral administration comprises an aqueous or non-aqueous sterile injection solution, an emulsion or a suspension. The dosage form suitable for rectal administration comprises a suppository or an enema. The dosage form suitable for transdermal administration comprises an ointment, a cream and a patch. The dosage form suitable for nasal administration comprises an aerosol, a spray and a nose drop The dosage form suitable for vaginal administration comprises a suppository, a plugging agent and a gel, a paste or a spray. Preferably, the crystalline forms of the present disclosure is especially suitable for preparing a tablet, a suspension, a capsule, a disintegrating tablet, an immediate release and controlled release tablet, and further preferably is a tablet, a suspension and a capsule.

The pharmaceutically acceptable excipient in the pharmaceutical composition is in the condition of a solid oral dosage form, including but not limited to: A diluent, such as starch, pregelatinized starch, lactose, powdery cellulose, microcrystalline cellulose, calcium hydrophosphate, tricalcium phosphate, mannitol, sorbitol, sugar and the like. An adhesive, such as arabic gum, guar gum, gelatin, polyvinylpyrrolidone, hydroxypropyl cellulose, hydroxypropyl methyl cellulose, polyethylene glycol and the like. A disintegrating agent, such as starch, sodium hydroxyacetate, pregelatinized starch, cross-linked povidone, cross-linked sodium carboxymethyl cellulose and colloidal silica. A lubricant, such as stearic acid, magnesium stearate, zinc stearate, sodium benzoate, sodium acetate and the the like. A glidants, such as colloidal silica and the like. A compound forming agent, such as various levels of cyclodextrin and resin. The release rate control agent, such as hydroxypropyl cellulose, hydroxymethyl cellulose, hydroxypropyl methyl cellulose, ethyl cellulose, methyl cellulose, methyl methacrylate, wax and the like. Other pharmaceutically acceptable excipients, including but not limited to: a film-forming agent, a plasticizer, a coloring agent, a flavoring agent, a viscosity regulator, a preservative, an antioxidant and the the like. Preferably, coating the tablet with a coating layer, for example, providing shellac isolation coating, sugar coating or polymer coating, wherein the coating layer comprises a polymer such as hydroxypropyl methyl cellulose, polyvinyl alcohol, ethyl cellulose, methacrylic acid polymer, hydroxypropyl cellulose or starch, and can also comprise an anti-sticking agent such as silicon dioxide, talcum powder, an emulsion agent such as titanium dioxide, a colorant such as an iron oxide colorant. In the case of a liquid oral dosage form, the appropriate excipient comprises water, oils, alcohols and glycols, a preservative, a stabilizer, a coloring agent and the like. The water or the non-water sterile suspension can contain a suspending agent and a thickening agent. The excipient that is suitable for the water-based suspension comprises synthetic rubber or natural rubber such as arabic gum, xanthium gum, alginate, glucan, sodium carboxymethyl cellulose, methylcellulose, polyvinylpyrrolidone or gelatin. In the case of parenteral administration, the excipient of the water or non-aqueous sterile injectable solution is generally sterile water, normal saline or a glucose aqueous solution, which can contain a buffering agent, an antioxidant, a bacteriostatic agent and a solute capable of enabling the pharmaceutical composition to be combined with blood.

Each excipient must be acceptable, and can be compatible with other ingredients in the formula and is harmless to a patient.

The pharmaceutically acceptable carrier in the pharmaceutical composition comprises, but is not limited to: single, double- or polysaccharide, sugar alcohol or another polyhydroxy compound. The appropriate carrier comprises sugar, starch and the like, such as lactose, sucrose, sorbitol sugar, mannitol, starch such as potato starch, corn starch or branched starch, cellulose derivatives and the like. The pharmaceutical composition can be obtained by methods known to those skilled in the art in the prior art. When preparing the pharmaceutical composition, the crystalline forms of the pharmaceutical composition is mixed with one or more pharmaceutically acceptable excipients, and mixed with one or more other active pharmaceutical ingredients. For example, the tablet, the capsule and the granule can be prepared through processes of mixing, granulating, tabletting or filling capsules. The powder is prepared by mixing active pharmaceutical ingredients and excipients which are ground into a proper size. The solution and the syrup can be prepared by dissolving the active pharmaceutical ingredients in a properly flavored water or aqueous solution. The suspension can be prepared by dispersing the active pharmaceutical ingredients in pharmaceutically acceptable carriers.

Particularly mentioned is the wet granulation process of solid formulations. Taking the wet granulation process for preparing tablets as an example, the process is: blending dry solids of active ingredients, fillers, adhesives, etc., wetting the mixture with a wetting agent such as water or alcohols, aggregating or granulating the wetted solid, continuing the wet granulation process until the required uniform particle size is obtained, and drying the obtained granules. Then mixing the dried granules with disintegrants, lubricants, anti-adhesives, etc., perform in tableting machine, optionally, coating the tablets with appropriate coating material.

Particularly mentioned is oral suspension. One advantage of the dosage form is that patients do not need to swallow solids, so it is particularly suitable for elders or children who have difficulties in swallowing solids, or patients with oral or throat injuries. Suspension is a two-phase system formed by dispersing solid particles in a liquid which can maintain their original solid forms in water or aqueous carriers in an oral suspension. Other ingredients in the oral suspension may include buffers, surfactants, viscosity regulators, preservatives, antioxidants, coloring agents, flavoring agents, taste masks, etc.

The co-crystals provided in the present disclosure have advantageous properties to produce the above dosage forms.

Furthermore, the present disclosure provides the use of co-crystal for preparing drugs treating cancer.

As used herein, the term "ancer" refers to a malignant or benign growth of cells in skin or in body organs, for example but without limitation, breast, prostate, lung, kidney, pancreas, stomach or bowel. A cancer tends to infiltrate into adjacent tissue and spread (metastasise) to distant organs, for example to bone, liver, lung or the brain. As used herein the term cancer includes both metastatic tumour cell types, such as but not limited to, melanoma, lymphoma, leukaemia, fibrosarcoma, rhabdomyosarcoma, and mastocytoma and types of tissue carcinoma, such as but not limited to, colorectal cancer, prostate cancer, small cell lung cancer and non-small cell lung cancer, breast cancer, pancreatic cancer, bladder cancer, renal cancer, gastric cancer, glioblastoma, primary liver cancer, ovarian cancer, prostate cancer and uterine leiomyosarcoma.

In the following examples, the test method is generally implemented according to a conventional condition or a condition that manufacturer recommends.

The abbreviations used in the disclosure are explained as follows:
XRPD: X-ray Powder Diffraction
DSC: Differential Scanning Calorimetry
TGA: Thermal Gravimetric Analysis
DVS: Dynamic Vapor Sorption
X-ray powder diffraction pattern in the present disclosure was acquired by a Panalytical Empyrean X-ray powder diffractometer. The parameters of the X-ray powder diffraction method of the present disclosure were as follows:
X-ray Reflection: Cu, Kα
Kα1 (Å): 1.540598; Kα2 (Å): 1.544426
Kα2/Kα1 intensity ratio: 0.50
Voltage: 45 (kV)
Current: 40 (mA)
Scan range: from 3.0 degree to 40.0 degree Differential scanning calorimetry (DSC) data in the present disclosure were acquired by a TA Q2000. The parameters of the differential scanning calorimetry (DSC) method of the present disclosure were as follow:
Heating rate: 10° C./min
Purge gas: nitrogen Thermal gravimetric analysis (TGA) data in the present disclosure were acquired by a TA Q5000. The parameters of the thermal gravimetric analysis (TGA) method of the present disclosure were as follow:
Heating rate: 10° C./min
Purge gas: nitrogen
Dynamic vapor sorption (DVS) data in the present disclosure were acquired by a SMS (Surface Measurement Systems Ltd.) DVS Intrinsic. The parameters of the dynamic vapor sorption (DVS) method of the present disclosure were as follow:
Temperature: 25° C.
Gas and flow rate: $N_2$, 200 mL/min
dm/dt: 0.002%/min
RH range: 0% RH to 95% RH Example 1

Process for Preparing Crystalline Form I:

26.6 mg of MEK162 was added into 4 mL acetonitrile/$H_2O$ (v:v=19:1), stirred at 50° C. for 30 min. Then 16.0 mg of LEE011 was added into the settled solution, stirred overnight and the settled solution was slowly cooled to 20° C., then the Form I was obtained.

Figure 2:
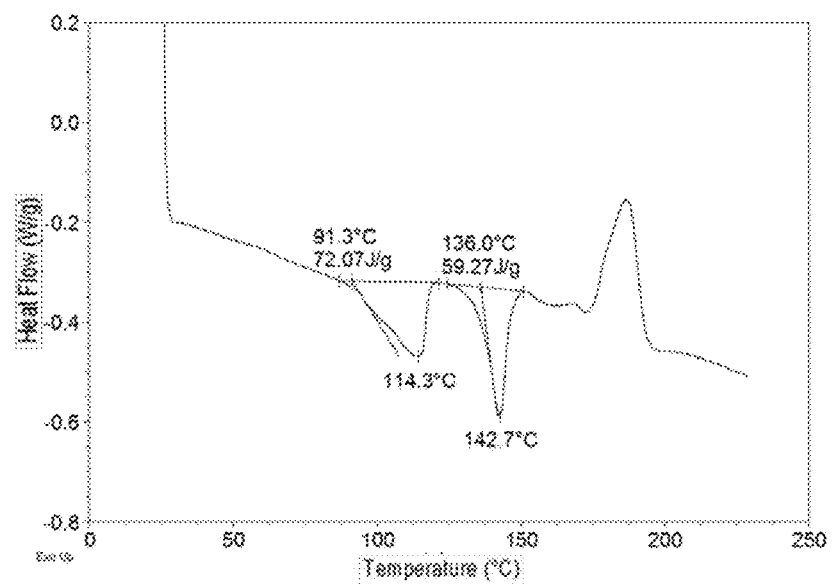
FIG. 2 shows a DSC thermogram of crystalline Form I obtained in Example 1.
Figure 3:
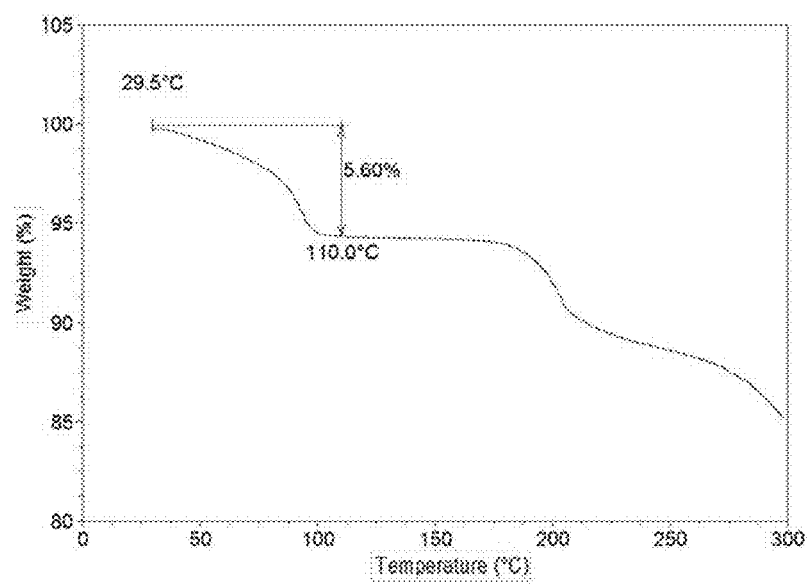
FIG. 3 shows a TGA thermogram of crystalline Form I obtained in Example 1.

The X-ray powder diffraction datas of the crystalline Form in this example were listed in Table 1. The X-ray powder diffraction (XRPD) pattern was displayed in FIG. 1, the DSC thermogram was displayed in FIG. 2, and the TGA thermogram was displayed in FIG. 3. As shown in FIG. 2, Form I in this example showed first endothermic peak when heated to around 86~95° C. and showed second endothermic peak when heated to around 130~142° C. As shown in FIG. 3, Form I in this example showed about 5~6% weight loss when heated to around 110° C.

TABLE 1

| 2theta | d spacing | intensity % |
|---|---|---|
| 7.46 | 11.85 | 15.77 |
| 8.29 | 10.67 | 20.26 |
| 10.37 | 8.53 | 54.57 |

TABLE 1-continued

| 2theta | d spacing | intensity % |
|---|---|---|
| 11.37 | 7.79 | 52.73 |
| 12.48 | 7.10 | 5.21 |
| 13.00 | 6.81 | 18.91 |
| 13.35 | 6.63 | 45.08 |
| 14.11 | 6.28 | 9.89 |
| 14.57 | 6.08 | 18.05 |
| 15.84 | 5.60 | 18.04 |
| 16.67 | 5.32 | 13.53 |
| 16.87 | 5.26 | 15.95 |
| 17.88 | 4.96 | 6.10 |
| 19.29 | 4.60 | 100.00 |
| 19.55 | 4.54 | 19.83 |
| 20.26 | 4.38 | 11.23 |
| 21.59 | 4.12 | 39.45 |
| 22.39 | 3.97 | 16.48 |
| 22.67 | 3.92 | 60.10 |
| 22.94 | 3.88 | 19.18 |
| 23.55 | 3.78 | 46.10 |
| 23.79 | 3.74 | 13.16 |
| 25.22 | 3.53 | 19.81 |
| 25.97 | 3.43 | 25.44 |
| 26.80 | 3.33 | 15.49 |
| 28.04 | 3.18 | 11.25 |
| 29.21 | 3.06 | 10.34 |
| 30.64 | 2.92 | 8.17 |
| 32.85 | 2.73 | 2.68 |
| 34.60 | 2.59 | 7.79 |

Example 2

Process for Preparing Form I:

9.7 mg of MEK162 and 1 mL of acetonitrile/$H_2O$ (v:v=1:1) were stirred at room temperature (25±3° C.) for 30 minutes, then 10.0 mg of LEE011 was added, stirred overnight and Form I was obtained.

The X-ray powder diffraction data of the crystalline Form in this example were listed in Table 2.

TABLE 2

| 2theta | d spacing | intensity % |
|---|---|---|
| 3.22 | 27.42 | 11.23 |
| 8.29 | 10.66 | 9.56 |
| 10.35 | 8.55 | 50.27 |
| 11.39 | 7.77 | 91.96 |
| 12.48 | 7.09 | 17.17 |
| 13.03 | 6.79 | 40.68 |
| 13.36 | 6.63 | 23.26 |
| 14.13 | 6.27 | 17.96 |
| 14.59 | 6.07 | 32.17 |
| 15.84 | 5.59 | 43.33 |
| 16.87 | 5.26 | 20.04 |
| 17.79 | 4.99 | 14.32 |
| 19.28 | 4.60 | 100.00 |
| 19.50 | 4.55 | 37.86 |
| 20.27 | 4.38 | 31.90 |
| 21.61 | 4.11 | 84.38 |
| 21.95 | 4.05 | 37.58 |
| 22.40 | 3.97 | 13.89 |
| 22.70 | 3.92 | 44.95 |
| 22.92 | 3.88 | 28.38 |
| 23.54 | 3.78 | 55.57 |
| 25.21 | 3.53 | 59.00 |
| 26.01 | 3.43 | 17.66 |
| 26.43 | 3.37 | 17.34 |
| 26.80 | 3.33 | 44.71 |
| 28.09 | 3.18 | 20.04 |
| 28.53 | 3.13 | 13.50 |
| 29.20 | 3.06 | 22.59 |
| 30.56 | 2.92 | 16.49 |
| 32.93 | 2.72 | 12.45 |

TABLE 2-continued

| 2theta | d spacing | intensity % |
|---|---|---|
| 33.62 | 2.67 | 5.92 |
| 34.68 | 2.59 | 4.91 |

Example 3

Process for Preparing Form I:

8.7 mg of MEK162 and 1 mL of ethanol/$H_2O$ (v:v=9:1) were stirred at room temperature (25±3° C.) for 30 minutes, then 8.5 mg of LEE011 was added, stirred overnight and the Form I was obtained.

The X-ray powder diffraction data of the crystalline Form in this example were listed in Table

TABLE 3

| 2theta | d spacing | intensity % |
|---|---|---|
| 3.14 | 28.18 | 13.45 |
| 7.45 | 11.87 | 19.86 |
| 8.26 | 10.70 | 22.91 |
| 10.33 | 8.56 | 100.00 |
| 11.35 | 7.80 | 89.00 |
| 13.33 | 6.64 | 52.60 |
| 14.56 | 6.09 | 8.95 |
| 15.59 | 5.68 | 15.70 |
| 15.86 | 5.59 | 12.65 |
| 16.72 | 5.30 | 6.96 |
| 19.23 | 4.61 | 61.00 |
| 19.49 | 4.55 | 33.72 |
| 20.23 | 4.39 | 9.01 |
| 21.57 | 4.12 | 38.33 |
| 21.97 | 4.05 | 15.48 |
| 22.37 | 3.97 | 13.19 |
| 22.68 | 3.92 | 34.85 |
| 22.91 | 3.88 | 23.68 |
| 23.51 | 3.78 | 66.75 |
| 25.14 | 3.54 | 11.63 |
| 26.00 | 3.43 | 12.70 |
| 26.44 | 3.37 | 10.37 |
| 27.40 | 3.26 | 4.58 |
| 28.01 | 3.19 | 10.62 |
| 29.20 | 3.06 | 11.69 |
| 30.45 | 2.94 | 5.02 |
| 31.48 | 2.84 | 4.93 |
| 32.94 | 2.72 | 4.88 |
| 33.70 | 2.66 | 4.78 |
| 34.66 | 2.59 | 8.45 |

Example 4

Process for Preparing Form II:

5.64 mg of Form I in the example 1 was heated to 135° C. at the rate of 5° C./min, balanced for 5 minutes at 135° C., then cooled to room temperature (25±3° C.), and Form II was obtained.

Figure 4:
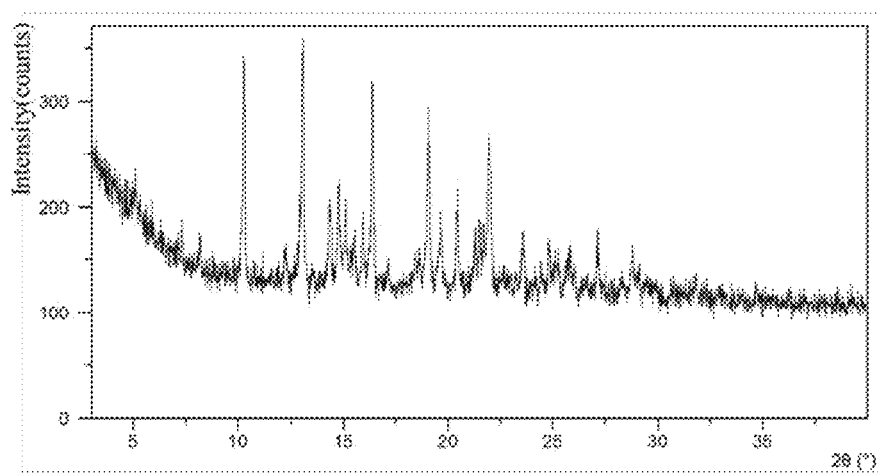
FIG. 4 shows an XRPD pattern of crystalline Form II obtained in Example 4.
Figure 5:
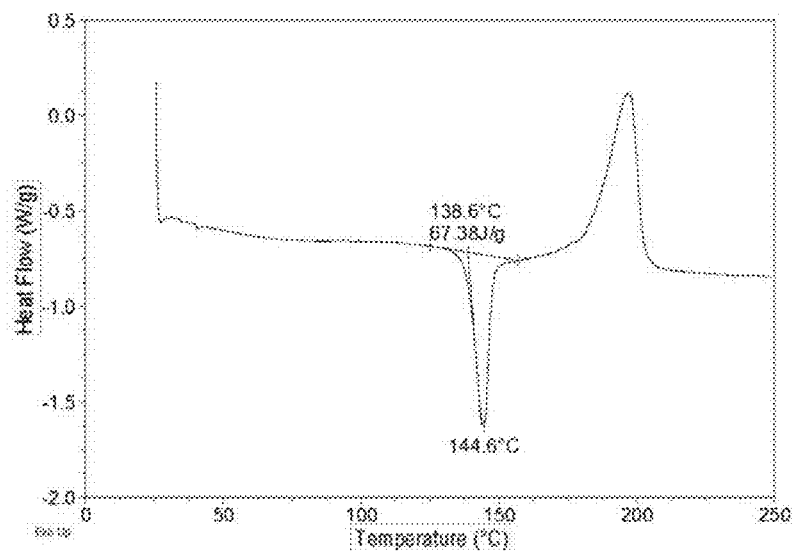
FIG. 5 shows a DSC thermogram of crystalline Form II obtained in Example 4.
Figure 6:
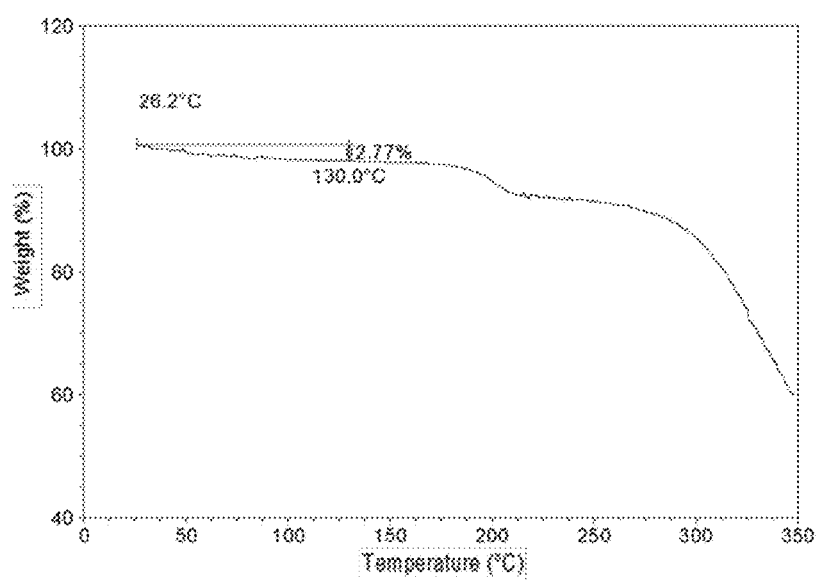
FIG. 6 shows a TGA thermogram of crystalline Form II obtained in Example 4.

The X-ray powder diffraction datas of the crystalline Form in this example were listed in Table 4. The X-ray powder diffraction (XRPD) pattern was displayed in FIG. 4, the DSC thermogram was displayed in FIG. 5 and TGA thermogram was displayed in FIG. 6. As shown in FIG. 5, Form II in this example showed an endothermic peak when heated to around 132~146° C. As shown in FIG. 6, Form II in this example showed about 2.6~2.9% weight loss when heated to around 130° C.

In this example, as shown in FIG. 5 and FIG. 6, there was little weight loss in TGA and no desolvation or dehydration peak in DSC, thus the Form II was speculated to be anhydrate.

In this example, since Form II can be obtained by heating co-crystal Form I, when the heating temperature is below the melting point, the mole ratio of co-crystal Form II is same as Form I.

TABLE 4

| 2theta | d spacing | intensity % |
|---|---|---|
| 10.28 | 8.60 | 88.40 |
| 12.24 | 7.23 | 10.87 |
| 13.08 | 6.77 | 100.00 |
| 14.38 | 6.16 | 28.82 |
| 14.77 | 6.00 | 40.14 |
| 15.11 | 5.86 | 32.45 |
| 15.54 | 5.70 | 21.55 |
| 15.94 | 5.56 | 26.07 |
| 16.40 | 5.41 | 82.48 |
| 19.08 | 4.65 | 73.82 |
| 19.66 | 4.52 | 30.54 |
| 20.44 | 4.34 | 36.32 |
| 21.30 | 4.17 | 23.50 |
| 21.49 | 4.14 | 28.93 |
| 21.94 | 4.05 | 61.50 |
| 23.56 | 3.78 | 26.06 |
| 24.82 | 3.59 | 19.24 |
| 25.77 | 3.46 | 13.53 |
| 27.12 | 3.29 | 26.26 |
| 28.77 | 3.10 | 17.81 |

Example 5

Process for preparing Form III:

327 mg of Form I in the example 1 was added into a 20 mL glass vial, and 15 mL of methanol was added to get a clear solution at room temperature (25±3° C.), 4.0 mL of filtrate was added into a 20 mL glass vial. The Form III was obtained when the solution was evaporated out slowly at room temperature (25±3° C.).

Figure 7:
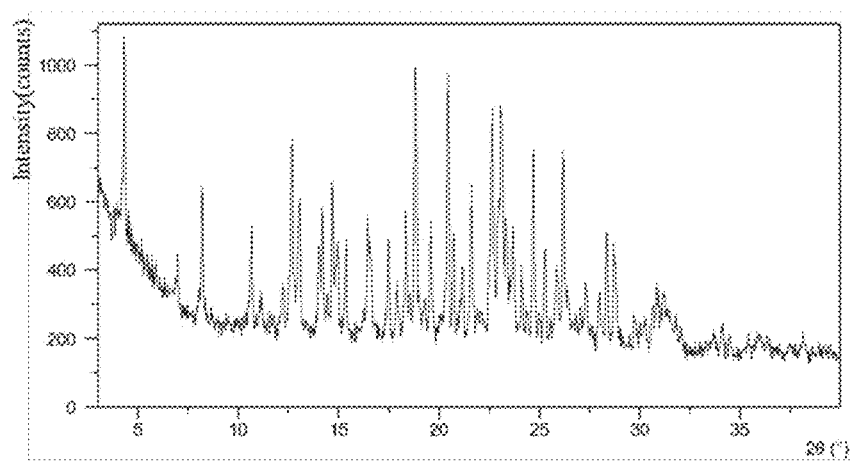
FIG. 7 shows an XRPD pattern of crystalline Form III obtained in Example 5.
Figure 8:
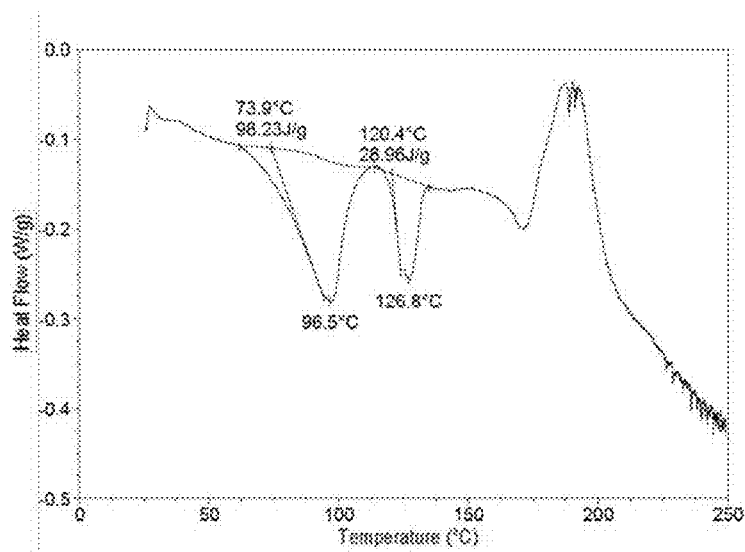
FIG. 8 shows a DSC thermogram of crystalline Form III obtained in Example 5.

The X-ray powder diffraction datas of the crystalline form in this example were listed in Table 5. The X-ray powder diffraction (XRPD) pattern was displayed in FIG. 7, the DSC thermogram was displayed in FIG. 8, and the TGA thermogram was displayed in FIG. 9. As shown in FIG. 8, Form III in this example showed first endothermic peak when heated to around 70~78° C., and showed second endothermic peak when heated to around 114~126° C.

Figure 9:
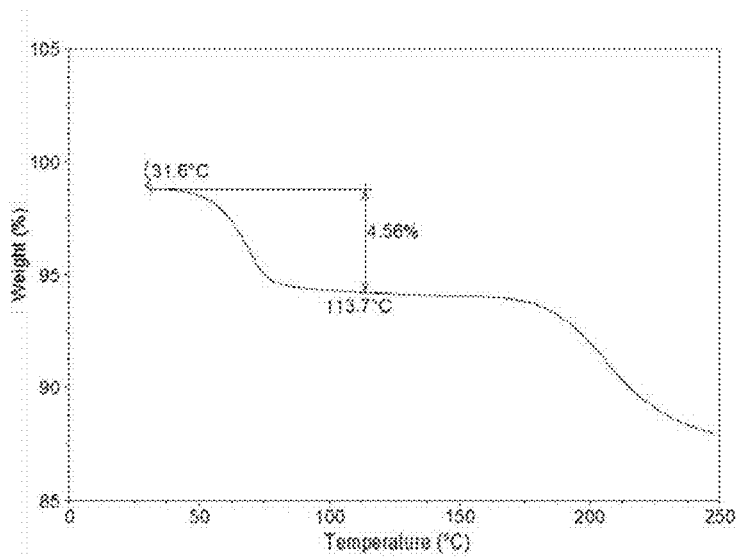
FIG. 9 shows a TGA thermogram of crystalline Form III obtained in Example 5.

As shown in FIG. 9, Form III in this example showed about 4.4~4.8% weight loss when heated to around 114° C.

Figure 24:
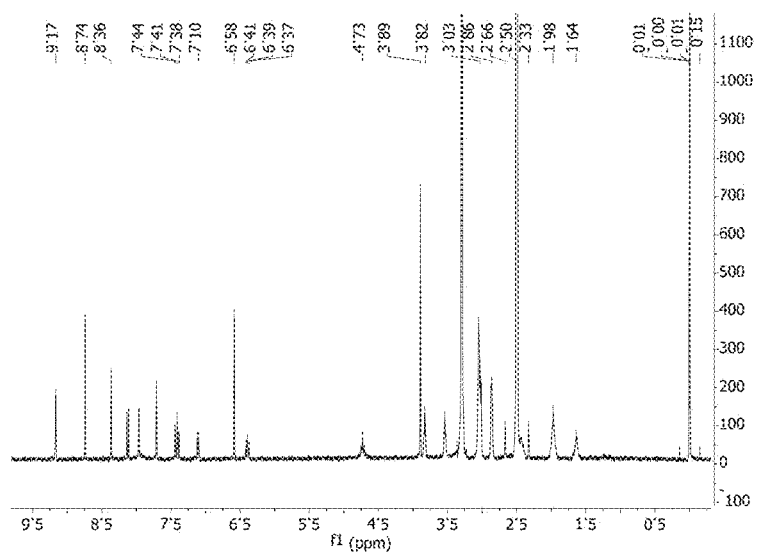
FIG. 24 shows a $^1$H NMR spectrum of crystalline Form III.

In this example, as shown in FIG. 8, FIG. 9 and FIG. 24, no solvent peak was detected in the NMR data. The water contain of Form III was speculated to be two moles according to the weight loss in TGA.

TABLE 5

| 2theta | d spacing | intensity % |
|---|---|---|
| 4.32 | 20.47 | 74.25 |
| 6.98 | 12.67 | 19.43 |
| 8.21 | 10.77 | 52.14 |
| 10.66 | 8.30 | 40.17 |
| 11.13 | 7.95 | 9.95 |
| 12.21 | 7.25 | 16.15 |
| 12.67 | 6.99 | 73.69 |
| 13.06 | 6.78 | 50.14 |
| 14.02 | 6.32 | 34.07 |
| 14.20 | 6.24 | 45.97 |
| 14.69 | 6.03 | 53.55 |
| 14.95 | 5.93 | 33.77 |
| 15.36 | 5.77 | 34.35 |
| 16.44 | 5.39 | 45.62 |

TABLE 5-continued

| 2theta | d spacing | intensity % |
|---|---|---|
| 17.47 | 5.08 | 36.63 |
| 17.90 | 4.95 | 19.28 |
| 18.35 | 4.84 | 49.50 |
| 18.83 | 4.71 | 100.00 |
| 19.60 | 4.53 | 40.25 |
| 20.45 | 4.34 | 98.38 |
| 20.73 | 4.28 | 39.01 |
| 21.17 | 4.20 | 26.77 |
| 21.61 | 4.11 | 59.12 |
| 22.65 | 3.93 | 82.63 |
| 23.09 | 3.85 | 87.13 |
| 23.33 | 3.81 | 45.39 |
| 23.69 | 3.76 | 44.45 |
| 24.11 | 3.69 | 27.57 |
| 24.70 | 3.60 | 66.81 |
| 25.26 | 3.53 | 32.21 |
| 25.87 | 3.44 | 25.25 |
| 26.19 | 3.40 | 73.11 |
| 27.31 | 3.27 | 20.97 |
| 27.98 | 3.19 | 17.86 |
| 28.35 | 3.15 | 40.40 |
| 28.73 | 3.11 | 31.97 |
| 29.74 | 3.00 | 8.68 |
| 30.76 | 2.91 | 12.65 |
| 34.09 | 2.63 | 8.82 |
| 36.11 | 2.49 | 4.11 |
| 38.15 | 2.36 | 5.57 |

Example 6

Process for Preparing Form III:

16.1 mg of Form I in the example 1 was added into 5 mL glass vial, and 2.0 mL of methanol was added to get a clear solution at room temperature (25±3° C.), 0.5 mL of filtrate was added into a 1.5 mL glass vial. The Form III was obtained when the solution was evaporated out slowly at room temperature (25±3° C.).

The X-ray powder diffraction data of the Form In this example were listed in Table 6.

TABLE 6

| 2theta | d spacing | intensity % |
|---|---|---|
| 4.32 | 20.47 | 79.71 |
| 6.95 | 12.72 | 13.82 |
| 8.21 | 10.78 | 28.88 |
| 10.62 | 8.33 | 47.81 |
| 11.16 | 7.93 | 14.53 |
| 12.22 | 7.25 | 25.47 |
| 12.67 | 6.99 | 99.86 |
| 13.02 | 6.80 | 38.93 |
| 14.21 | 6.23 | 50.16 |
| 14.68 | 6.04 | 29.07 |
| 14.95 | 5.93 | 47.33 |
| 15.37 | 5.76 | 39.88 |
| 16.45 | 5.39 | 39.87 |
| 17.50 | 5.07 | 20.03 |
| 17.86 | 4.97 | 0.91 |
| 18.35 | 4.84 | 39.70 |
| 18.82 | 4.72 | 88.33 |
| 19.59 | 4.53 | 28.72 |
| 20.46 | 4.34 | 92.09 |
| 20.73 | 4.28 | 22.28 |
| 21.18 | 4.20 | 14.16 |
| 21.64 | 4.11 | 32.19 |
| 22.65 | 3.93 | 89.85 |
| 23.11 | 3.85 | 100.00 |
| 23.68 | 3.76 | 32.80 |
| 24.11 | 3.69 | 25.42 |
| 24.70 | 3.60 | 45.04 |
| 25.29 | 3.52 | 31.45 |
| 25.86 | 3.44 | 8.01 |

TABLE 6-continued

| 2theta | d spacing | intensity % |
|---|---|---|
| 26.20 | 3.40 | 57.19 |
| 27.97 | 3.19 | 17.82 |
| 28.34 | 3.15 | 34.63 |
| 28.75 | 3.11 | 38.49 |
| 31.18 | 2.87 | 40.13 |
| 31.77 | 2.82 | 20.65 |
| 34.17 | 2.62 | 6.27 |
| 35.85 | 2.51 | 4.81 |
| 38.11 | 2.36 | 13.92 |

Example 7

Process for Preparing Form III:

50.0 mg of MEK162 and 49.3 mg of LEE011 were added into a 20 mL glass vial, and 8.0 mL of methanol was added to get a clear solution at room temperature (25±3° C.), 4.0 mL of filtrate was added into a 20 mL glass vial. The Form III was obtained when the solution was evaporated out slowly at room temperature (25±3° C.).

The X-ray powder diffraction data of the Form In this example were listed in Table 7.

TABLE 7

| 2theta | d spacing | intensity % |
|---|---|---|
| 4.31 | 20.51 | 88.46 |
| 6.95 | 12.71 | 19.46 |
| 8.22 | 10.76 | 61.59 |
| 10.63 | 8.33 | 26.74 |
| 12.67 | 6.99 | 60.62 |
| 13.07 | 6.77 | 40.81 |
| 14.03 | 6.31 | 35.47 |
| 14.21 | 6.23 | 38.51 |
| 14.70 | 6.03 | 64.45 |
| 15.36 | 5.77 | 37.63 |
| 16.50 | 5.37 | 33.24 |
| 17.48 | 5.07 | 35.31 |
| 18.34 | 4.84 | 41.49 |
| 18.83 | 4.71 | 97.35 |
| 19.60 | 4.53 | 37.68 |
| 20.46 | 4.34 | 100.00 |
| 20.73 | 4.29 | 45.38 |
| 21.17 | 4.20 | 36.02 |
| 21.63 | 4.11 | 70.32 |
| 22.65 | 3.93 | 91.83 |
| 23.10 | 3.85 | 85.91 |
| 23.34 | 3.81 | 51.75 |
| 23.70 | 3.75 | 44.02 |
| 24.71 | 3.60 | 72.82 |
| 25.29 | 3.52 | 34.34 |
| 26.20 | 3.40 | 83.77 |
| 28.33 | 3.15 | 40.73 |
| 28.71 | 3.11 | 45.12 |
| 31.21 | 2.87 | 19.49 |

Example 8

(I) Assessment of Mole Ratio of MEK162 and LEE011 of Form I:

The mole ratio of co-crystal of MEK162 and LEE011 was tested with HPLC by dissolved in methanol solution, and the result indicated that the mole ratio of MEK162 and LEE011 was 1:1, as shown in Table 8.

TABLE 8

| Compound | Co-crystal of MEK162 and LEE011 |
|---|---|
| Concentration of MEK162 (mmol/L) | 0.128 |
| Concentration of LEE011 (mmol/L) | 0.131 |
| Mole ratio | 1:1 |

(II) Assessment of Mole Ratio of MEK162 and LEE011 of Form III:

1.504 mg of Form III prepared in the example 5 of the present disclosure was added into a glass vial, then 10 mL of methanol solution was added to get a clear solution. The mole ratio of MEK162 and LEE011 was tested and calculated by HPLC instrument, and the results were listed in the Table 9.

TABLE 9

| Compound | MEK162/LEE011 constituents |
|---|---|
| Concentration of MEK162 (mmol/L) | 0.157 |
| Concentration of LEE011 (mmol/L) | 0.153 |
| Mole ratio | 1:1 |

Example 9

Figure 10:
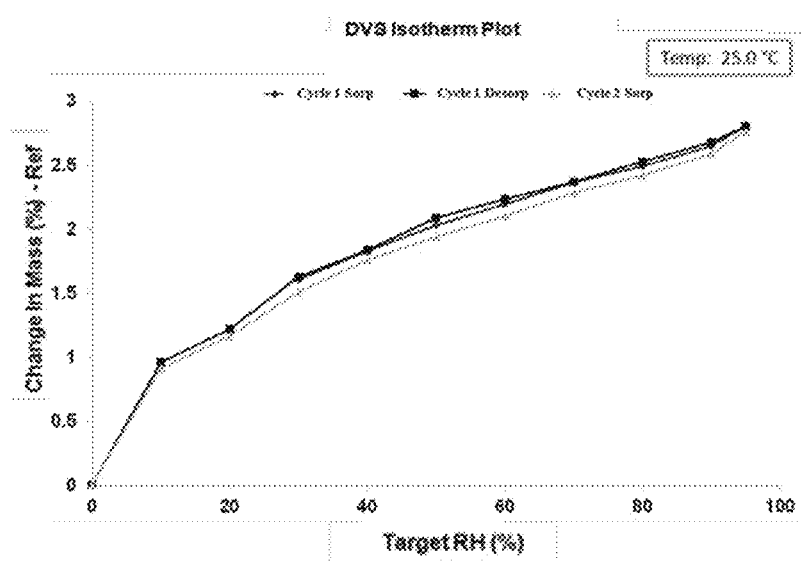
FIG. 10 shows a DVS plot of crystalline Form I.
Figure 11:
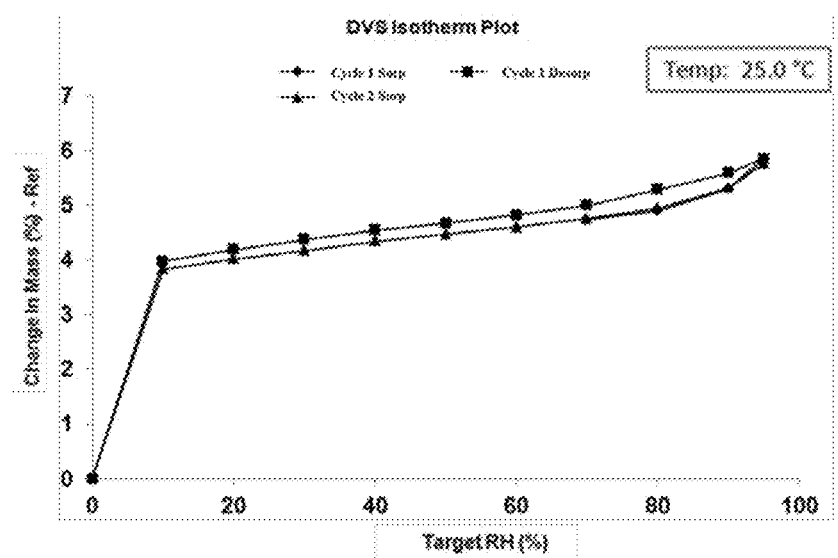
FIG. 11 shows a DVS plot of crystalline Form III.

(I) Hygroscopicity Assessment of Form I:

10 mg of Form I of example 1 was tested using dynamic vapor sorption (DVS). The result was listed in Table. 10. The DVS isotherm plot of Form I was depicted in FIG. 10.

TABLE 10

| Weight increment (%) | Relative Humidity | |
|---|---|---|
| | weight uptake from 10% to 80% relative humidity | Weight uptake from 10% to 95% relative humidity |
| Form I | 2.28% | 2.77% |

Figure 19:
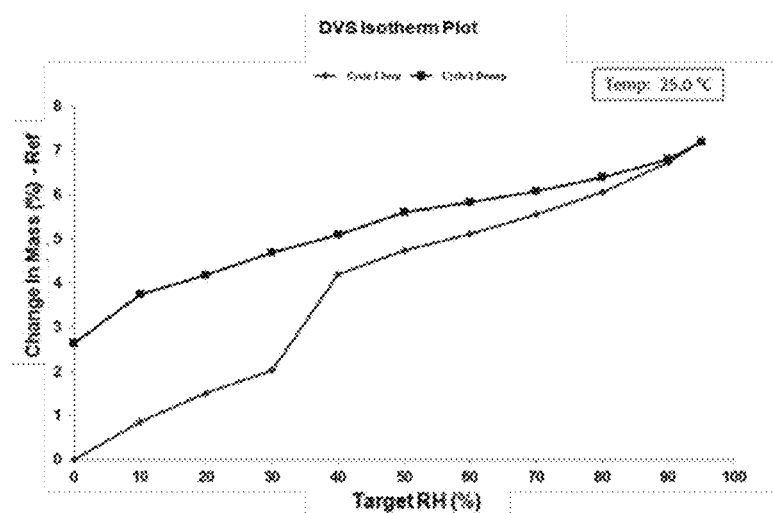
FIG. 19 shows a DVS plot of crystalline Form II.

(II) Hygroscopicity assessment of Form II:

10 mg of Form II of example 4 was tested using dynamic vapor sorption (DVS). The result was listed in Table. 11. The DVS isotherm plot of Form I was depicted in FIG. 19.

TABLE 11

| Weight increment (%) | Relative Humidity | |
|---|---|---|
| | weight uptake from 10% to 80% relative humidity | Weight uptake from 10% to 95% relative humidity |
| Form II | 5.20% | 6.35% |

Figure 20:
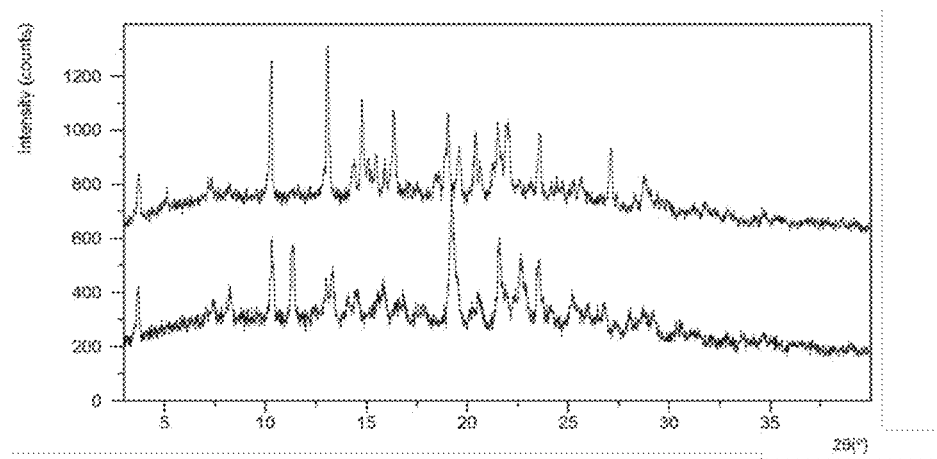
FIG. 20 shows an XRPD pattern of crystalline Form II after DVS experiment (the pattern above is XRPD pattern of crystalline Form I and the below one is XRPD pattern of crystalline Form II after DVS experiment)

The Form II converted to Form I after DVS test confirmed by XRPD, as shown in FIG. 20.

(III) Hygroscopicity Assessment of Form III:

10 mg of Form III of example 5 was tested using dynamic vapor sorption (DVS). The result was listed in Table 12. The DVS isotherm plot of Form I was depicted in FIG. 13.

TABLE 12

| Weight increment (%) | Relative Humidity | |
|---|---|---|
| | weight uptake from 10% to 80% relative humidity | Weight uptake from 10% to 95% relative humidity |
| Form III | 1.12% | 1.93% |

About hygroscopicity characterization description and definition of hygroscopicity (Chinese Pharmacopoeia 2010 edition appendix XIX J Drug hygroscopic test guidelines)

deliquescent: sufficient water is absorbed to form a liquid;

very hygroscopic: increase in mass is equal to or greater than 15%;

hygroscopic: increase in mass is less than 15% and equal to or greater than 2%;

slightly hygroscopic: increase in mass is less than 2% and equal to or greater than 0.2%.

no or almost no hygroscopic: increase in mass is less than 0.2%.

The result indicated that the weight uptake of Form I of the present disclosure was 2.28% when the relative humidity increased from 10% to 80% and balanced, showing little hygroscopic. The weight uptake was 2.77% when the relative humidity increased from 10% to 95% and balanced, indicating that the Form I was difficultly deliquescent under the effect of high humidity.

The result indicated that the weight uptake of Form III of the present disclosure was 1.12% when the relative humidity increased from 10% to 80% and balanced, showing slightly hygroscopic. The weight uptake was 1.93% when the relative humidity increased from 10% to 95% and balanced, indicating that the Form III was difficultly deliquescent under the effect of high humidity.

Example 10

(I) Stability Assessment of Form I:

Two samples of Form I of the example 1 in the present disclosure were stored with dish open under 25° C./60% RH (relative humidity) and 40° C./75% RH separately, the XRPD were tested after 14 days, and the results were listed in table 13.

TABLE 13

Figure 12:
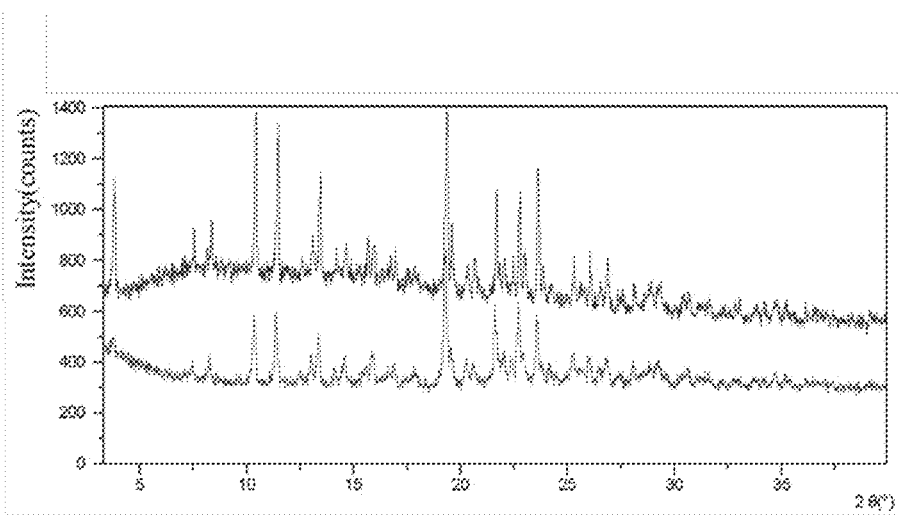
FIG. 12 shows an XRPD overlay pattern of crystalline Form I before and after storing at 25° C./60% RH for 14 days (the pattern above is after storing and the below one is before storing)
Figure 13:
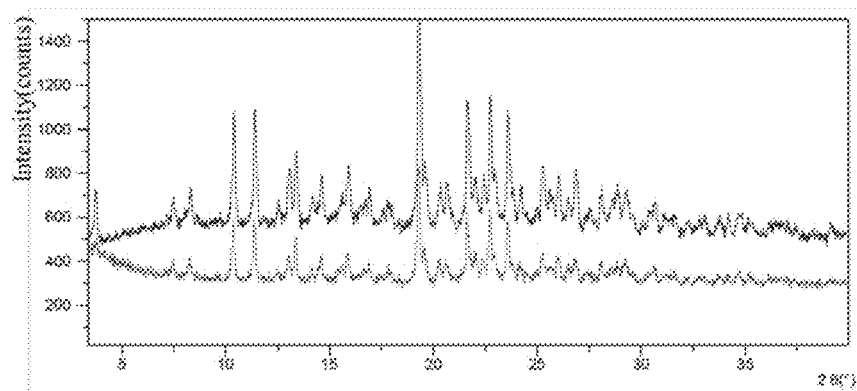
FIG. 13 shows an XRPD overlay pattern of crystalline Form I before and after storing at 40° C./75% RH for 14 days (the pattern above is after storing and the below one is before storing)

| Initial form | Condition | Storage time | Form change |
|---|---|---|---|
| Form I | 25° C./60% RH | 14 days | Form I remained unchanged (as shown in FIG. 12) |
| Form I | 40° C./75% RH | 14 days | Form I remained unchanged (as shown in FIG. 13) |

The results indicated that Form I of the present disclosure remained unchanged after 14 days under the conditions of 25° C./60% RH and 40° C./75% RH.

(II) Stability Assessment of Form II:

Two samples of Form II of the example 4 in the present disclosure were stored opened under 25(±3°) C/25% RH (relative humidity), the XRPD was tested after 2 days, and the results were listed in table 14.

TABLE 14

Figure 21:
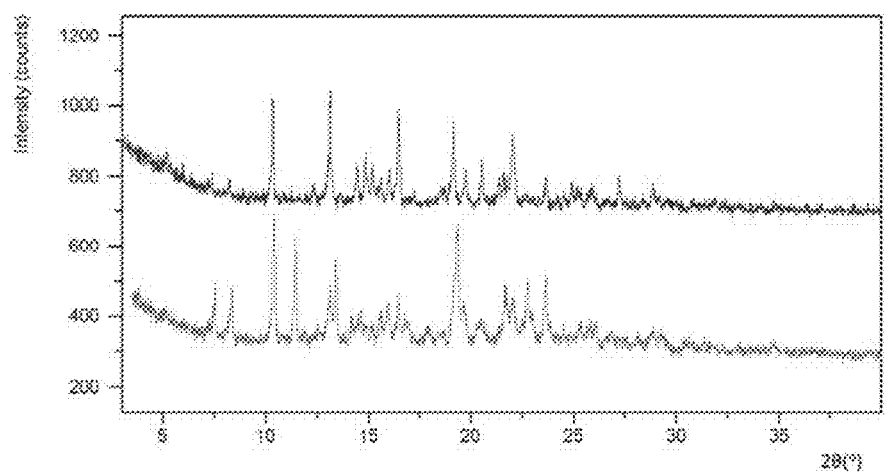
FIG. 21 shows an XRPD overlay pattern of crystalline Form II before and after storing at 25° C./60% RH for 2 days (the pattern above is before storing and the below one is after storing)

| Initial form | Condition | Storage time | Form change |
|---|---|---|---|
| Form II | 25(±3)° C./25% RH | 2 days | Form II converted to Form I (as shown in FIG. 21) |

The results indicated that Form II of the present disclosure changed to Form I after 2 days under the condition of 25(±3°) C/25% RH.
(III) Stability Assessment of Form III:
Two samples of Form III of the example 5 in the present disclosure were stored with dish open under 25° C./60% RH and 40° C./75% RH separately, the XRPD was tested after 30 days, and the results were listed in table 15.

TABLE 15

Figure 14:
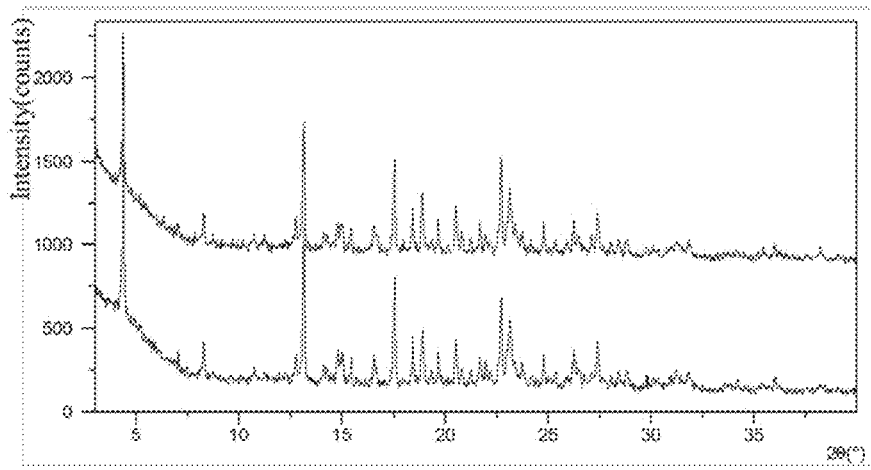
FIG. 14 shows an XRPD overlay pattern of crystalline Form III before and after storing at 25° C./60% RH for 30 days (the pattern above is before storing and the below one is after storing)
Figure 15:
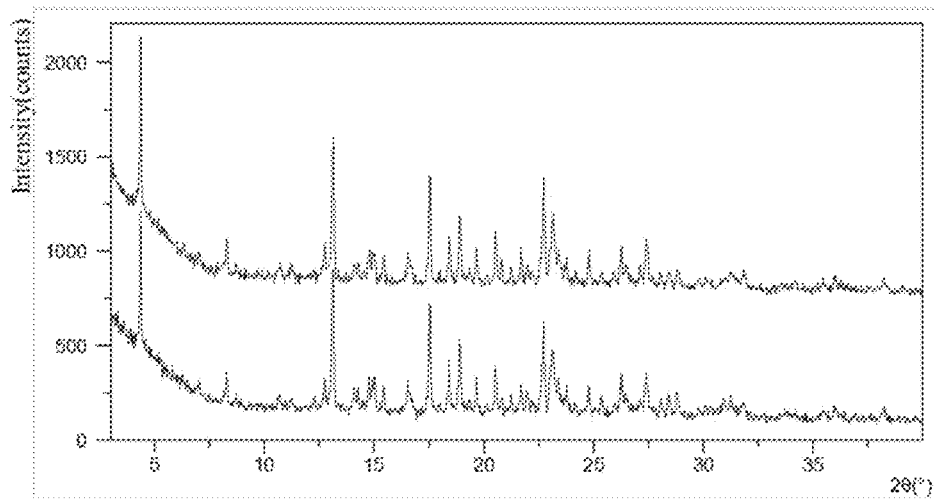
FIG. 15 shows an XRPD overlay pattern of crystalline Form III before and after storing at 40° C./75% RH for 30 days (the pattern above is before storing and the below one is after storing)

| Initial form | Condition | Storage time | Form change |
|---|---|---|---|
| Form III | 25° C./60% RH | 30 days | Form III remained unchanged (as shown in FIG. 14) |
| Form III | 40° C./75% RH | 30 days | Form III remained unchanged (as shown in FIG. 15) |

The results indicated that Form III of the present disclosure remained unchanged after 30 days under the conditions of 25° C./60% RH and 40° C./75% RH.

Example 11

Figure 22:
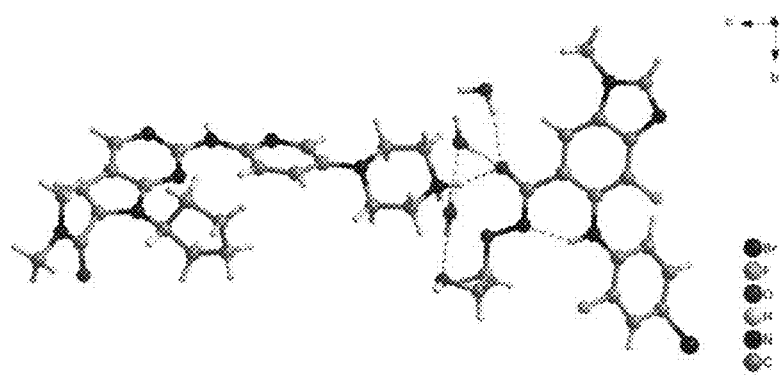
FIG. 22 shows a schematic diagram of an asymmetric structure unit of crystalline Form I.
Figure 23:
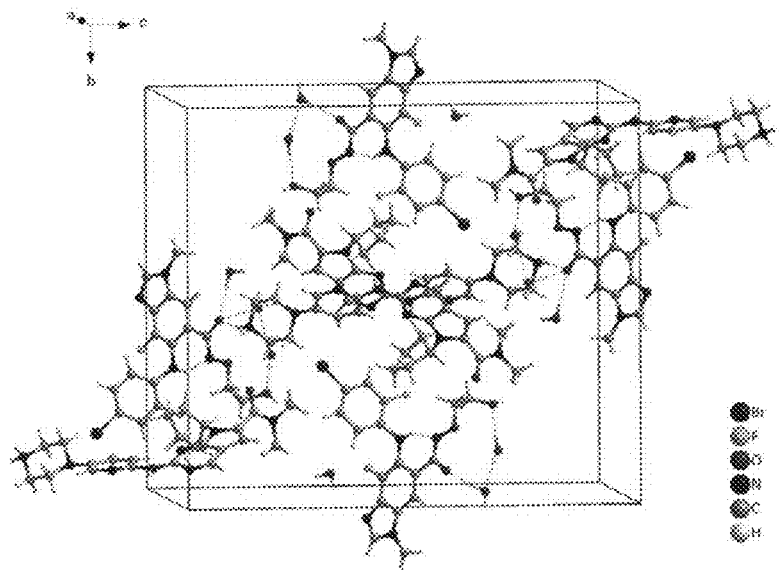
FIG. 23 shows a unit cell diagram of crystalline Form I.

Single Crystal Study of Form I
Single crystal X-ray diffractometer: Bruker D8 Venture
X-ray source: Model: TURBO X-RAY SOURCE high intensity microfocusing rotating anode generator
　　Wavelength: Mo/K$_\alpha$ ($\lambda$=0.71073)
　　Power: 2.5 KW
Detector: PHOTON 100 model CMOS 2D detector
Goniometer: Three-axis ($\omega$, $2\theta$, $\varphi$) goniometer
Test temperature: 153.15 K
Computer programs for structure analysis: Initial solution: ShelXT (direct method)
Refinement: ShelXL 2014 (least square method)
5.3 mg of co-crystal Form I in example 1 was dissolved into 4 mL of THF/H$_2$O (1:3) system to get a clear solution and filtered, and the solution was placed under room temperature for slow evaporation, then Form I single crystal was obtained after 1 month.
Molecular formula: $C_{40}H_{45}BrF_2N_{12}O_4 \cdot 3H_2O$
Molecular weight: 929.83
Color of crystalline form: colorless and transparent
Shape of crystalline form: long rod-like
Crystal system: monoclinic crystal system
Space group: P2$_1$/c
Unit cell dimensions: a=7.2846(13) Å
　　b=23.349(4) Å
　　c=25.612(5) Å
　　$\alpha$=90°
　　$\beta$=106.000(6)°
　　$\gamma$=90°
Volume of unit cell: V=4187.5(13) Å$^3$
Z (number of molecular formula in unit cell): 4
Calculated density: 1.475 g/cm$^3$
　　Description of structure: the single crystal diffraction and structural analysis indicated that the crystalline form belonged to monoclinic crystal system, P2$_1$/c space group, and the unit cell dimensions were {a=7.2846(13) Å, b=23.349(4) Å, c=25.612(5) Å; $\alpha$=90°, $\beta$=106.000(6)°, $\gamma$=90°; V=4187.5(13) Å$^3$}. The asymmetric structural unit of this crystalline form contained an MEK162 anion or molecule, a LEE011 cation or molecule, three water molecules. The unit cell of this crystalline form contained four MEK162 anions or molecules, four LEE011 cations or molecules, twelve water molecules; its asymmetric structural unit was depicted in FIG. 22 and the schematic diagram of unit cell is depicted in FIG. 23.

Example 12

Figure 16:
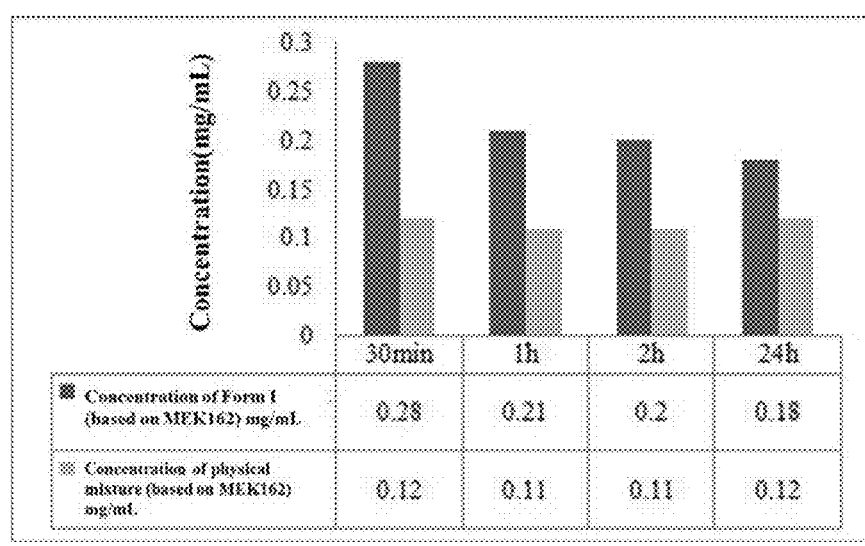
FIG. 16 shows a comparison chart of the solubility of crystalline Form I and physical mixture in SGF.
Figure 17:
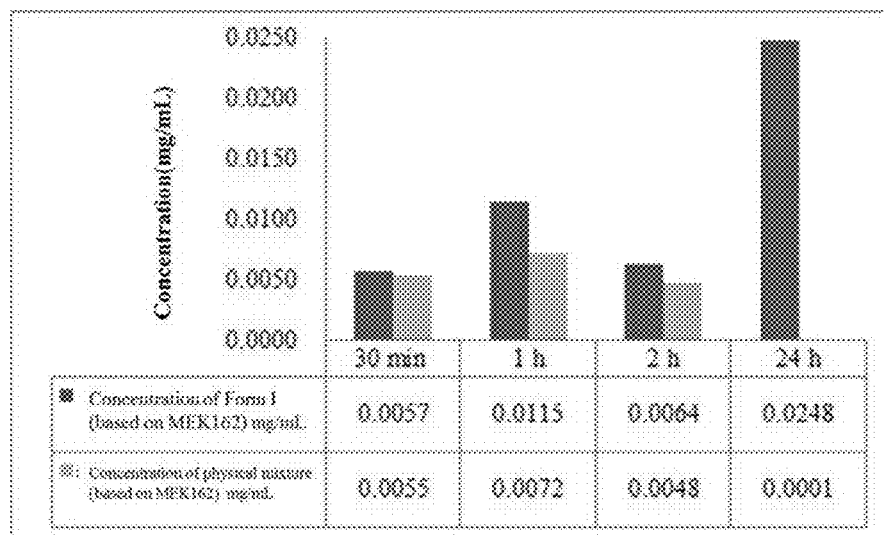
FIG. 17 shows a comparison chart of the solubility of crystalline Form I and physical mixture in FaSSIF.

Solubility Comparison Study of Form I and Physical Mixture:
Form I of example 1 and sample of equimolar physical mixture of LEE011 and MEK162 were added into SGF (pH1.8, simulated gastric fluid) and FaSSIF (pH6.5, fasting state of simulated intestinal fluid) to get saturated solutions. The MEK162 concentration in the saturated solution was measured with high performance liquid chromatography (HPLC) after 30 minutes, 1 hour, 2 hours and 24 hours. The solubility comparison (based on the concentration of MEK162) in these two samples are as shown in FIG. 16 (in SGF) and FIG. 17 (in FaSSIF)
The above comparison results indicated that the solubility of Form I of the present disclosure is higher than that of equimolar physical mixture in the SGF and FaSSIF after 30 minutes, 1 hour, 2 hours and 24 hours.

Example 13

Figure 18:
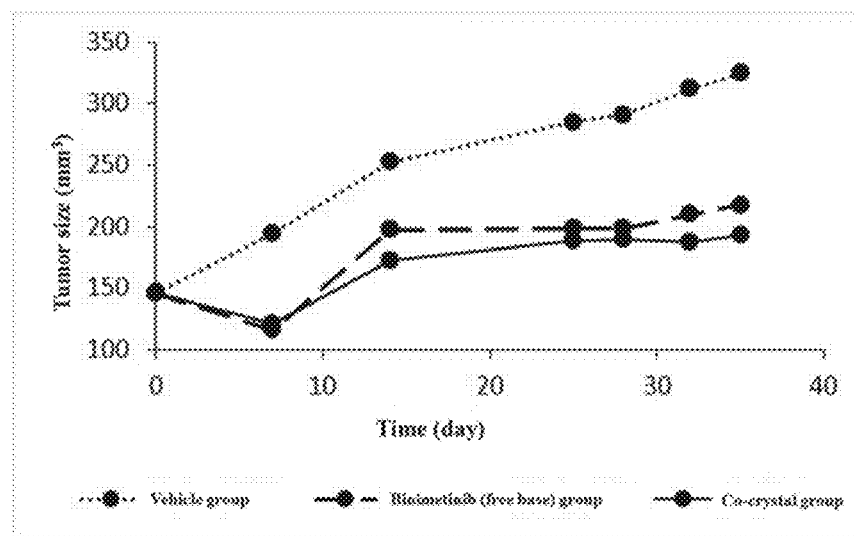
FIG. 18 shows a comparison chart of the in-vivo effectiveness of crystalline Form I and single component of MEK162 free base for treating melanoma.

Evaluation for In Vivo Efficacy
Investigations on the in vivo effectiveness of MEK162 free base single component, co-crystalline Form I of MEK162 and LEE011 (1:1) in the treatment of melanoma were conducted. Subjects were BALB/C female nude mice which were transplanted melanoma with NRAS mutation. Animal models were HuPrime® Xenograft model. Tumor fragments from stock mice inoculated with selected primary human melanoma tissues were harvested and used for inoculation into BALB/C nude mice. Each mouse was inoculated subcutaneously. Mice were randomly allocated into different experimental groups according to their tumor size. Each group consisted of 8 mice. The day of randomization was denoted as day 0. The test articles were administered to the tumor-bearing mice from day 1 through day 35. Tumor size was measured twice weekly. Tumor growth inhibition of MEK162 single component and co-crystal of MEK162-LEE011 were evaluated. The dosage of MEK162 single compound is 3.5 mg·kg$^{-1}$ (calculated as free base), twice a day. The dosage of co-crystal of MEK162-LEE011 was 7 mg·kg$^{-1}$ (calculated as co-crystal anhydrate form), twice a day. Vehicle group was 0.5% HPMC and 1% Tween 80 aqueous solution, twice a day.
The results (as shown in FIG. 18) indicated that the tumor size of mice in the MEK162-LEE011 co-crystal group were smaller than mice in the MEK162 single component group, showing antitumor effect of co-crystal was better than single component of MEK162.
Pharmacokinetics
Investigations on the pharmacokinetic characteristics of MEK162 free base single compound (group A), equimolar physical mixture of MEK162 and LEE011 succinate (group B) and co-crystal Form I of MEK162-LEE011 (group C) in the rats were conducted. Male SD rats with standard weight were chosen as experimental objects, three rats in a group and were orally administrated. The dosage in group A was 5 mg·kg$^{-1}$ (calculated as free base), the dosages of two components in group B were both 5 mg·kg$^{-1}$ (calculated as free base), the dosage in group C was 10 mg·kg$^{-1}$ (calculated as co-crystal anhydrate form), and dosage of these two components was around 5 mg·kg$^{-1}$ (calculated as free base) as calculated by molecular weight.

The results indicated that even though the dosage was similar in each group, to some extent, physical mixture in group B and co-crystal in group C had higher exposure of MEK162 comparing with group A which only MEK162 was given. Area under the drug time curve (AUC$_{0\text{-}inf}$) was 16439±5461 ng·h·mL$^{-1}$ in group B, 21926±5875 ng·h·mL$^{-1}$ in group C, which was about 1.5 and 1.9 times as much as that in group A (AUC$_{0\text{-}inf}$: 11325±895 ng·h·mL$^{-1}$). When MEK162 and LEE011 were co-administrated, the latter was expected to have certain improvement on the exposure of the former, especially after co-crystal administration, AUC$_{0\text{-}inf}$ of MEK162 increased significantly; comparing co-crystal administration in group C with physical mixing administration in group B, the exposure of MEK162 also increased, the former was about 1.3 times as much as latter.

In addition, the time take to reach maximum concentration (T$_{max}$) were almost equal (group A: 0.25 h, group B: 0.33 h, group C: 0.25 h), the maximum concentration of blood drug (C$_{max}$) of MEK162 after co-crystal administration in group C was 10145±2392 ng·mL$^{-1}$, comparing with C$_{max}$ of MEK162 after administered alone in group A was 3242±576 ng·mL$^{-1}$, the C$_{max}$ was improved by nearly 3 times, while there was no obvious change in group B (C$_{max}$: 71±630 ng·mL$^{-1}$)

In conclusion, both the UC$_{0\text{-}inf}$ and C$_{max}$ of MEK162 had different degrees of improvement after an MEK162 and LEE011 co-crystal administration, and bioavailability of MEK162 was increased to a certain extent.

The examples described above are only for illustrating the technical concepts and features of the present disclosure, and intended to make those skilled in the art being able to understand the present disclosure and thereby implement it, and should not be concluded to limit the protective scope of this disclosure. Any equivalent variations or modifications according to the spirit of the present disclosure should be covered by the protective scope of the present disclosure.

What is claimed is:

1. A co-crystal of a CDK inhibitor and an MEK inhibitor, wherein the structure of the co-crystal is shown as formula (I):

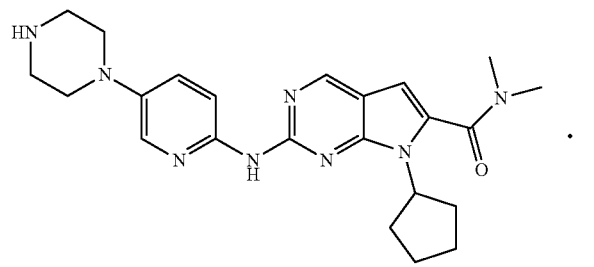

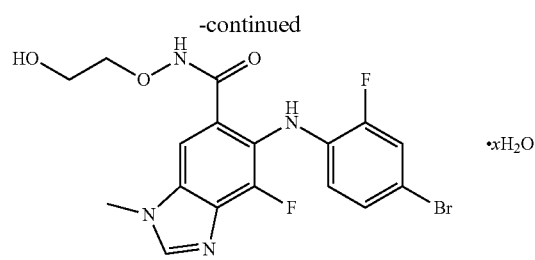

x is a number between 0 and 3.

2. The co-crystal according to claim 1, wherein x is a number of 0, 1, 2 or 3.

3. The co-crystal according to claim 1, wherein the co-crystal is hydrate Form I, having an X-ray powder diffraction pattern comprising the following 2theta values measured using CuKα radiation: 19.3°±0.2°, 22.7°±0.2°, 10.4°±0.2°.

4. The co-crystal according to claim 3, wherein the X-ray powder diffraction pattern of Form I further shows one or two or three characteristic peaks at 2theta values of 11.4°±0.2°, 23.6°±0.2°, 13.4°±0.2°.

5. The co-crystal according to claim 3, wherein the X-ray powder diffraction pattern of Form I further shows one or two or three characteristic peaks at 2theta values of 21.6°±0.2°, 26.0°±0.2°, 8.3°±0.2°.

6. The co-crystal according to claim 3, wherein the Form I contains 0.5-3 moles of water.

7. The co-crystal according to claim 1, wherein the co-crystal is anhydrous Form II, having an X-ray powder diffraction pattern comprising the following 2theta values measured using CuKα radiation: 13.1°±0.2°, 10.3°±0.2°, 16.4°±0.2°.

8. The co-crystal according to claim 7, wherein the X-ray powder diffraction pattern of Form II further shows one or two or three characteristic peaks at 2theta values of 19.1°±0.2°, 21.9°±0.2°, 14.8°±0.2°.

9. The co-crystal according to claim 7, wherein the X-ray powder diffraction pattern of Form II further shows one or two or three characteristic peaks at 2theta values of 20.4°±0.2°, 15.1°±0.2°, 19.7°±0.2°.

10. The co-crystal according to claim 1, wherein the co-crystal is crystalline Form III, having an X-ray powder diffraction pattern comprising the following 2theta values measured using CuKα radiation: 18.8°±0.2°, 20.5°±0.2°, 23.1°±0.2°.

11. The co-crystal according to claim 10, wherein the X-ray powder diffraction pattern of Form III further shows one or two or three characteristic peaks at 2theta values of 22.6°±0.2°, 4.3°±0.2°, 12.7°±0.2°.

12. The co-crystal according to claim 10, wherein the X-ray powder diffraction pattern of Form III further shows one or two or three characteristic peaks at 2theta values of 26.2°±0.2°, 24.7°±0.2°, 21.6°±0.2°.

13. The co-crystal according to claim 10, wherein the Form III contains 2~3 moles of water.

14. A process of preparing the co-crystal in claim 3, wherein LEE011 and MEK162 are mixed in a mixture of ethanol or acetonitrile and water and Form I is obtained by evaporation, stirring and cooling.

15. The process of preparing the co-crystal according to claim 14; LEE011 and MEK162 is mixed in the mixture of ethanol or acetonitrile and water at a temperature of 0-50° C.; the content of MEK162 in said mixture containing water is 6~10 mg/mL; the mass ratio of LEE011 and MEK162 is 1:0.9~2.

16. The process of preparing the co-crystal in claim 7, wherein the process comprises step 1 or step 2:
  step 1: LEE011 and MEK162 are mixed in a mixture of ethanol and water or acetonitrile and water and Form I is obtained by evaporation, stirring and cooling, and then Form II is obtained by dehydrating Form I;
  step 2: LEE011 and MEK162 are mixed in acetonitrile or ethanol, and then the Form II is obtained by evaporation, stirring and cooling.

17. The process of preparing the co-crystal according to claim 16, wherein the dehydrating in step 1 is at a temperature of 130~140° C.

18. The process of preparing the co-crystal in claim 10 wherein the process comprises step 1 or step 2:
  Step 1: LEE011 and MEK162 are mixed in a mixture of ethanol and water or acetonitrile and water and Form I is obtained by evaporation, stirring and cooling, Form I is mixed in methanol, and then Form III is obtain by evaporation;
  Step 2: LEE011 and MEK162 are mixed in methanol, and then Form III is obtain by evaporation.

19. The process of preparing the co-crystal according to claim 18, wherein the content of Form I in said methanol in step 1 is 8~25 mg/mL; in step 1, Form I is mixed in methanol, and then Form III is obtain by evaporation; the mass ratio of LEE011 and MEK162 in step 2 is 1:0.9~1.1; the content of MEK162 in methanol in step 2 is 6~7 mg/mL.

* * * * *